(12) United States Patent
Scruggs

(10) Patent No.: US 8,956,664 B2
(45) Date of Patent: Feb. 17, 2015

(54) METHODS AND COMPOSITIONS FOR TREATING MUCOSITIS

(71) Applicant: Salient Pharmaceuticals Incorporated, Houston, TX (US)

(72) Inventor: Richard M. Scruggs, Houston, TX (US)

(73) Assignee: Salient Pharmaceuticals Incorporated, Houston, TX (US)

( * ) Notice: Subject to any disclaimer, the term of this patent is extended or adjusted under 35 U.S.C. 154(b) by 0 days.

(21) Appl. No.: 13/657,585

(22) Filed: Oct. 22, 2012

(65) Prior Publication Data

US 2013/0101645 A1 Apr. 25, 2013

Related U.S. Application Data

(60) Provisional application No. 61/549,574, filed on Oct. 20, 2011.

(51) Int. Cl.
*A61K 33/06* (2006.01)
*A61K 45/06* (2006.01)
*A61K 35/02* (2006.01)
*A61K 33/12* (2006.01)

(52) U.S. Cl.
CPC .............. *A61K 45/06* (2013.01); *A61K 33/12* (2013.01); *A61K 33/06* (2013.01); *A61K 35/02* (2013.01)
USPC ........................... 424/682; 424/683; 424/684

(58) Field of Classification Search
None
See application file for complete search history.

(56) References Cited

U.S. PATENT DOCUMENTS

| 4,942,042 | A | 7/1990 | Bhargava et al. |
| 5,165,946 | A | 11/1992 | Taylor et al. |
| 5,178,832 | A | 1/1993 | Phillips et al. |
| 5,192,547 | A | 3/1993 | Taylor |
| 5,698,226 | A | 12/1997 | Fielden |
| 2008/0026079 | A1 | 1/2008 | Carpenter et al. |
| 2008/0038337 | A1 | 2/2008 | Li |

FOREIGN PATENT DOCUMENTS

| CN | 1326745 A | 12/2001 |
| EP | 1747775 A1 | 1/2007 |
| RU | 2329815 C1 | 7/2008 |
| UA | 30790 U | 3/2008 |
| WO | WO 86/06633 A1 | 11/1986 |
| WO | WO 2005/112881 A1 | 12/2005 |
| WO | WO 2006/067945 A1 | 6/2006 |
| WO | WO 2007/011825 A2 | 1/2007 |
| WO | WO 2008/013630 A2 | 1/2008 |
| WO | WO 2008/013631 A2 | 1/2008 |
| WO | WO 2009/087091 A2 | 7/2009 |
| WO | WO 2010/012720 A1 | 2/2010 |
| WO | WO 2010012720 A1 * | 2/2010 |

OTHER PUBLICATIONS

Keefe (Updated clinical practice guidelines for the prevention and treatment of mucositis, 109 Cancer 820 (2007).*
Wang (Short-term safety evaluation of processed calcium montmorillonite clay (NovaSil) in humans, 22 Food Additives & Contaminants 270 (2005).*
International Search Report from PCT Application No. PCT/US2012/061197, mailed on Mar. 14, 2013, application now published as WO2013/059728 on Apr. 25, 2013.
Abdel-Wahhab et al., "Potential protective effect of HSCAS and bentonite against dietary aflaxicosis in rat: with special reference to chromosomal aberrations", Natural Toxins, vol. 6, No. 5, pp. 211-218 (1998).
Abo-Norag et al., "Influence of hydrated sodium calcium aluminosilicate and virginiamycin on aflatoxicosis in broiler chicks", Poult. Sci., vol. 74, pp. 626-632 (1995).
Afriyie-Gyawu, "Safety and efficacy of NovaSil clay as a dietary supplement to prevent aflatoxicosis", Dissertation pp. 1-178 (2004).
Afriyie-Gyawu et al., "Chronic toxicological evaluation of dietary novasil clay in sprague-dawley rats", Food Additives, and Contaminants, vol. 22, No. 3, pp. 259-269 (2005).
Afriyie-Gyawu et al., "Prevention of zearalenone-induced hyperestrogenism in prepubertal mice", J. Environ. Health, vol. 68, pp. 353-368 (2005).
Afriyie-Gyawu et al., "NovaSil clay intervention in Ghanaians at high risk for aflatoxicosis: I. study design and clinical outcomes", Food Additives and Contaminants, vol. 25, No. 1, pp. 76-87 (2008).
Bailey et al, "Efficacy of montmorillonite clay (NovaSil PLUS) for protecting full-term broilers from aflatoxicosis", Journal of Applied Poultry Research, vol. 15, No. 2, pp. 198-206 (2006).
Bingham et al., "Potential for dietary protection against the effects of aflatoxins in animals", J. Am. Vet. Med. Assoc., vol. 222, No. 5, 591-596 (2003).
Bingham et al., "Identification and reduction of urinary aflatoxin metabolites in dogs", Food and Chemical Toxicology, vol. 42, pp. 1851-1858 (2004).
Brunner et al., "Nonparametric analysis of longitudinal data factorial experiments", John Wiley, New York, N.Y., 8 pages (2002) Title page and Table of Contents only.
Cizmas et al., "Toxicity characterization of complex mixtures using biological and chemical analysis in preparation for assessment of mixture similarity", Environ. Sci. Technol., vol. 38, No. 19, pp. 5127-5133 (2004).
Clark et al, "In vitro studies on the use of clay, clay minerals and charcoal to absorb bovine rotavirus and bovine rotavirus and bovine coronavirus", Veterinary Microbiology, Elsevier BV, NL, vol. 63, No. 2-4, pp. 137-146 (1998).
Dembinski et al., "The use of bentonite of polish production in gastrointestinal disease of newborn calves" Medycyna Weterynaryjna, Warzaw, PL, vol. 41, No. 6, pp. 359-362 (1985).
Desjeux et al., "Agents for diarrhoea in children", The Lancet, vol. 337, pp. 924-925 (1991).

(Continued)

*Primary Examiner* — H. Sarah Park
(74) *Attorney, Agent, or Firm* — Judy M. Mohr; McDermott Will & Emery LLP

(57) ABSTRACT

The present disclosure relates generally to the field of mucositis. More particularly, methods and compositions for treating, ameliorating and/or preventing mucositis are provided by administering a clay to the subject in need.

17 Claims, 6 Drawing Sheets

(56) References Cited

OTHER PUBLICATIONS

Gange et al., "Variability of molecular biomarker measurements from nonlinear calibration curves", Cancer Epidemiol. Biomarkers Prev., vol. 5, pp. 57-61 (1996).

Gonzalez et al. "Anti-inflammatory effect of diosmectite in hapten-induced colitis in the rat", British Journal of Pharmacology, vol. 141, pp. 951-960 (2004).

Grant et al., "Modified langmuir equation for S-shaped and multisite isotherm plots", Langmuir, vol. 14, No. 15, pp. 4292-4299 (1998).

Grant and Phillips, "Isothermal adsorption of aflatoxin B1 on HSCAS", J. Ag. Fd. Chem., vol. 46, pp. 599-605 (1998).

Harvey et al., "Suppression of serum iron binding capacity and bone marrow cellularity in pigs fed aflatoxin", Bull. Envir. Contam. Toxicol., vol. 40, pp. 576-583 (1988).

Harvey et al., "Progression of aflatoxicosis in growing barrows", Am. J. Vet. Res. vol. 49, No. 4, pp. 482-487 (1988).

Harvey et al., "Evaluation of diets cocontaminated with aflatoxin and ochratoxin fed to growing pigs", Am. J. Vet. Res., vol. 50, No. 8, pp. 1400-1405 (1989).

Harvey et al., "Effects of aflatoxin, deoxynivalenol, and their combinations in the diets of growing pigs", Am. J. Vet. Res., vol. 50, No. 4, pp. 602-607 (1989).

Harvey et al., "Prevention of aflatoxicosis by addition of hydrated sodium calcium aluminosilicate to the diets of growing barrows", Am J. Vet. Res., vol. 50, No. 3, pp. 416-420 (1989).

Harvey et al., "Effects of treatment of growing swine with aflatoxin and T-2 toxin", Am. J. Vet. Res., vol. 51, No. 10, pp. 1688-1693 (1990).

Harvey et al., "Effects on aflatoxin $M_1$ residues in milk by addition of hydrated sodium calcium aluminosilicate to aflatoxin-contaminated diets of dairy cows", Am. J. Vet. Res., vol. 52, No. 9, pp. 1556-1559 (1991).

Harvey et al., "Efficacy of zeolitic ore compounds on the toxicity of aflatoxin to growing broiler chickens", Avian Diseases, vol. 37, No. 1, pp. 67-73 (1993).

Harvey et al., "Comparison of two hydrated sodium calcium aluminosilicate compounds to experimentally protect growing barrows from aflatoxicosis", J. Vet. Diagn. Invest., vol. 6, pp. 88-92 (1994).

Herrerra et al., "The efficacy of sand-immobilized organoclays as filtration bed materials for bacteria", Food Microbiol., vol. 21, No. 1, pp. 1-10 (2004).

Hombrink et al., "Prevention of radiation-induced diarrhea by smectite. Results of a double-blind randomized, placebo controlled multicenter study", Strahlentherapie Onkologie, vol. 176, No. 4, pp. 173-179 (2000).

Huebner et al., "Molecular charaterization of high affinity, high capacity clays for the equilibrium sorption of ergotamine", Food Additives and Contaminants, vol. 16, No. 4, 159-171 (1999).

Huff et al., "Efficacy of hydrated sodium calcium aluminosilicate to reduce the combined toxicity of aflatoxin and ochratoxin A", Poult. Sci., vol. 71, pp. 64-69 (1992).

Jolly et al., "Determinants of aflatoxin levels in Ghanaians: sociodemographic factors, knowledge of aflatoxin and food handling and consumption practices", Int. J. Hyg. Environ. Health, vol. 209, pp. 345-358 (2006).

Kubena et al., "Efficacy of a hydrated sodium calcium aluminosilicate to reduce the toxicity of aflatoxin and T-2 toxin", Poult. Sci., vol. 69, No. 1078-1086 (1990).

Kubena et al., "Diminution of aflatoxicosis in growing chickens by the dietary addition of a hydrated, sodium calcium aluminosilicate", Poult. Sci., vol. 69, pp. 727-735 (1990).

Kubena et al., "Effects of hydrated sodium calcium aluminosilicate on growing turkey poults during aflatoxicosis", Poult. Sci., vol. 70, No. 8, pp. 1823-1830 (1991).

Kubena et al., "Efficacy of hydrated sodium calcium aluminosilicate to reduce the toxicity of aflatoxin and diacetoxyscirpenol", Poult. Sci., vol. 72, No. 1, pp. 51-59 (1993).

Chen et al., "Observation of effects of smectite powder in treatment of leukemia patients with chemotherapy-induced oral mucositis", Nanfang Journal of Nursing, Online article accessed on Jan. 17, 2013, Retreived from the internet: <URL: http//en.cnki.com.cn/Article_en/CJFDTOTAL-NFHL200401023.htm>, 1 page (2004) Abstract only.

Dodd et al., "Radiation-induced mucositis: a randomized clinical trial of micronized sucralfate versus salt & soda mouthwashes", Cancer Invest., vol. 21, No. 1, pp. 21-33 (2003) Abstract only.

International Search Report from related PCT Patent Application No. PCT/US2012/061206 mailed on Jan. 24, 2013.

International Search Report from related PCT Patent Application No. PCT/US2012/061385 mailed on Feb. 28, 2013.

Keefe et al., "Updated clinical practice guidelines for the prevention and treatment of mucositis", Cancer, vol. 109, No. 5, pp. 820-831 (2007).

Liu, "Curative effect of metronidazole gargle and smectite powder on oral mucositis in patients with chronic obstructive pulmonary disease", Modern Clinical Nursing, Online article accessed on Jan. 17, 2013, Retrieved from the internet: <URL: http://en.cnki.com.cn/Article_en/CJFDTOTAL-XDLH200701015.htm> 1 page (2007) Abstract only.

Kubena et al., "Effect of hydarted sodium calcium aluminosilicates on aflatoxicosis in broiler chicks", Poult. Sci., vol. 72, No. 4, pp. 651-657 (1993).

Lemke et al., "Adsorption of zearalenone by organophilic montmorillonite clay", J. Ag. Fd. Chem., vol. 46, pp. 3789-3796 (1998).

Lemke et al., "Investigation of organophilic montmorillonite clay inclusion in zearalenone-contaminated diets using the mouse uterine weight bioassay", J. Toxicol. Environ. Health., vol. 62, pp. 243-258 (2001).

Lemke et al., "Development of a multi-tiered approach in the in vitro prescreening of clay-based enterosorbents", Animal Feed Sci. Technol., vol. 93, pp. 17-29 (2001).

Li "Dispersible montmorillonite tablets for treating e.g. acute and chronic diarrhea, gastritis, esophagitis, colitis, inflammation caused by gastrointestinal reflux, and irritable bowel syndrome" WPI/Thomson, AN: 2006-019993, 4 pages, Nov. 23, 2005.

Lopez et al., "Visual estimation of aflatoxin production in peanut with *Aspergillus* norsolorinic acid mutants", Peanut Sci., vol. 25, pp. 92-99 (1998).

Madkour et al., "Smectite in acute diarrhea in children: a double blind placebo-controlled clinical trial", Journal of Pediatric Gastroenterology and Nutrition, vol. 17, pp. 176-181 (1993).

NOVASIL™ PLUS Aluminosilicate Feed Additive, product information, 2 pages, Online article accessed on Aug. 24, 2008 from URL:http://trouwusa.newmind.co.uk/dbimgs/PRODINFORNovaSILPlus pdf>.

Ogilvie et al., "Acute and short-term toxicoses associated with the administration of doxorubicin to dogs with malignant tumors", J. Am. Vet. Med. Assoc., vol. 195, No. 11, pp. 1584-1587 (1989).

Phillips et al., "Hydrated sodium calcium aluminosilicate: a high affinity sorbent for aflatoxin", Poult. Sci., vol. 67, No. 2, pp. 243-247 (1988).

Phillips et al., "Prevention of aflatoxicosis in farm animals via selective chemisorption of aflatoxin", In Mycotoxins, Cancer and Health, vol. 1, pp. 223-237 (1990).

Phillips et al., "Detection and detoxification of aflatoxins: prevention of aflatoxicosis and aflatoxin residues with hydrated sodium calcium aluminosilicate", Vet. Human Toxicol., vol. 32 Supplement, pp. 15-19 (1990).

Phillips et al., "Approaches to reduction of aflatoxins in foods and feeds", In The Toxicology of Aflatoxins: Human Health, Veterinary, and Agricultural Significance, Eaton and Groopman, eds, Academic Press, NY, pp. 383-406 (1994).

Phillips et al., "Selective chemisorption and detoxification of aflatoxins by phyllosilicate clay", Natural Toxins, vol. 3, No. 4, pp. 204-213 (1995).

Phillips, "Dietary clay in the chemoprevention of aflatoxin-induced disease", Toxicological Sciences, vol. 52 Supplement, pp. 118-126 (1999).

Phillips et al., "Characterization of clay-based enterosorbents for the prevention of aflatoxicosis", Mycotoxins and Food Safety, Advances in Experimental Medicine and Biology, vol. 504, pp, 157-173 (2002).

(56) References Cited

OTHER PUBLICATIONS

Phillips et al., "The potential of aflatoxin sequestering clay", Barug et al., eds., *The Mytotoxin Factbook*, Wageningen Academic Publishers, the Netherlands, pp. 329-346 (2006).

Phillips et al., "Reducing human exposure to aflatoxin through use of clay: A review", Food Additives and Contaminants, vol. 25, No. 2, pp. 134-145 (2008).

Pimpukdee et al., "Aflatoxin-induced toxicity and depletion of hepatic vitamin A in young boiler chicks: protection of chicks in the presence of low levels of NovaSil Plus™ in the diet", Poult. Sci., vol. 83, pp. 737-744 (2004).

Ramu et al., "Adsorption of cholera and heat-labile *Escherichia coli* enterotoxins by various adsorbents: an in vitro study", J. Ed. Protect., vol. 60, No. 4, pp. 358-362 (1997).

Safe et al., "Synthesis and characterization of hydroxylated polychlorinated biphenyls (PCBs) identified in human serum", Chemosphere, vol. 31, No. 4, pp. 3017-3023 (1995).

Sarr et al., "Effects of phyllosilicate clay on the metabolic profile of aflatoxin $B_1$ in Fischer-344 rats", Toxicol., Lett., vol. 75, pp. 145-151 (1995).

Smith et al., "Dietary hydrated sodium calcium aluminosilicate reduction of aflatoxin M1 residue in dairy goat milk and effects on milk production and components", J. Anim. Sci., vol. 72, No. 3, pp. 677-682 (1994).

Szajewska et al.; "Meta-Analysis: Smectite in the treatment of acute infectious diarrhoea in children", Aliment Pharmacol. Ther., vol. 23, No. 2, pp. 217-227 (2006).

Wang et al., "Temporal patterns of aflatoxin-albumin adducts in hepatitis B surface antigen-positive and antigen-negative residents of Daxin, Qidong county, Peoples Republic of China", Cancer Epidemiol. Biomarkers Prev., vol. 5, pp. 253-261 (1996).

Wang et al., "Aflatoxin exposure and risk of hepatocellular carcinoma in Taiwan", Int. J. Cancer, vol. 67 pp. 620-625 (1996).

Wang et al., "Protective alterations in phase 1 and 2 metabolism of aflatoxin $B_1$ by oltipraz in residents of Qidong, Peoples Republic of China", J. Natl. Cancer Inst., vol. 91, No. 4, pp. 347-354 (1999).

Wang and Groopman; "DNA damaged by mytotoxins"; Mutat. Res., vol. 424, pp. 167-181 (1999).

Wang et al., "Development of aflatoxin $B_1$-lysine adduct monoclonal antibody for human exposure studies", Appl. Environ. Microbiol., vol. 67, No. 6, pp. 2712-2717 (2001).

Wang et al., "Hepatocellular carcinoma and aflatoxin exposure in Zhiqing village, Fusui county, Peoples Republic of China", Cancer Epidemial Biomarkers Prev., vol. 10, pp. 143-146 (2001).

Wang. et al., "Short-term safety evaluation of processed calcium montmorillonite clay (NovaSil) in humans", Food Additives and Contaminants, vol. 22, No. 3, pp. 270-279 (2005).

Wang, "NovaSil clay intervention in Ghanaians at high risk for aflatoxicosis: efficacy evaluations on aflatoxin biomarkers and vitamins A & E", Food Additives and Contaminants, Accepted (2007).

Wang et al., "NovaSil clay intervention in Ghanaians at high risk for aflatoxicosis: II. Reduction in biomarkers of aflatoxin exposure in blood and urine", Food Addit. Contam. Part A Chem. Anal. Control Expo. Risk Assess, vol. 25, No. 5, pp. 622-634 (2008).

Washburn and Phillips, "Development of a field-practical assay for water-solvated chlorophenols", J. Hazard. Mat., vol. 41, pp. 371-381 (1995).

Wiles et al., "Matrix-immobilized organoclay for the sorption of polycylic aromatic hydrocarbons and pentachlorophenol from groundwater", Chemosphere, vol. 59, pp. 1455-1464 (2005).

Wiles et al., "Toxicological evaluation and metal bioavailability in pregnant rats following exposure to clay minerals in the diet", Journal of Toxicolgy and Environmental Health, Part A, vol. 67, pp. 863-874. (2004).

Williams et al., "Human aflatoxicosis in developing countries: a review of toxicology, exposure, potential health consequences and interventions", Am. J. Clin. Nutr., vol. 80, pp. 1106-1122 (2004).

Yao-Zong et al., "Comparative efficacy of diactahedral smectite (Smecta) and a probiotic preparation in chronic functional diarrhoea", Dig. Liver Dis., vol. 36, No. 12, pp. 824-848 (2004).

Yen et al., "Best evidence topic report. smectite for acute diarrhoea in children", Emerg. Med. Journal, vol. 23, No. 1, pp. 65-66 (2006).

Zaid et al., "Attapulgite in the treatment of acute diarrhoea: a double-blind placebo-controlled study", J. Diarrhoeal Dis. Res., vol. 13, No. 1, pp. 44-46 (1995).

Chen et al., "Observation of effects of smectite powder in treatment of leukemia patients with chemotherapy-induced oral mucositis", Nanfang Journal of Nursing, Online article accessed on Dec. 5, 2013, Retreived from the internet: <URL: http//en.cnki.com.cn/Article_en/CJFDTOTAL-NFHL200401023.htm>, 3 pgs. (2004) Abstract only.

Groopman et al., "Molecular dosimetry in rat urine of aflatoxin-N7-guanine and other aflatoxin metabolites by multiple monoclonal antibody affinity chromatography and immunoaffinity/high performance liquid chromatography", Cancer Res., vol. 52, pp. 267-274 (1992).

Lin et al., "Effect of montmorillonite powder mixed with iodine glycerin on chemotherapy-induced oral mucositis", Journal of Nursing, Online article accessed on Dec. 5, 2013, Retreived from the internet: <URL: http://en.cnki.com.cn/Article_en/CJFDTOTAL-NFHL201006026.htm>, 2 pgs. (2010) Abstract only.

Rateau et al., "A histological, enzymatic and water-electrolyte study of the action of smectite, a mucoprotective clay, on experimental infectious diarrhoae in the rabbit", Current Medical Research and Opinions, vol. 8, No. 4, pp. 233-241 (1982).

Remington's Pharmaceutical Sciences 17th Edition. Alfonso Gennaro editor, Mack Publishing Company Easton, Pennsylvania 18042, Chapter 68, Pharmaceutical Necessities, pp. 1278-1320 (1985).

Remington's Pharmaceutical Sciences 17th Edition. Alfonso Gennaro editor, Mack Publishing Company, Easton, Pennsylvania 18042, Chapter 84, Solutions, Emulsions, Suspensions and Extractives, pp. 1492-1517 (1985).

Yang et al., "Clinical prevention and control of radioactive oral mucosa injury by montmorillonite powder and self gargle mouthwash", Journal of Clinical and Experimental Medicine, Online article accessed on Dec. 5, 2013, Retreived from the internet: <URL: http//en.cnki.com.cn/Article_en/CJFDTOTAL-SYLC200902022.htm>, 1 page (2009) Abstract only.

Ye, "Clinical analysis of 71 cases with oral mucositis induced by tumer radiochemotherapy with montmorillonite powder", Journal of Beihua University (Natural Science), Online article accessed on Dec. 5, 2013, Retreived from the internet: <URL: http//en.cnki.com.cn/Article_en/CJFDTOTAL-ZLYY200903012.htm>,4 pgs. (2009) Abstract only.

US 2008/0084763 A1, 01/2008, Phillips et al. (withdrawn)

\* cited by examiner

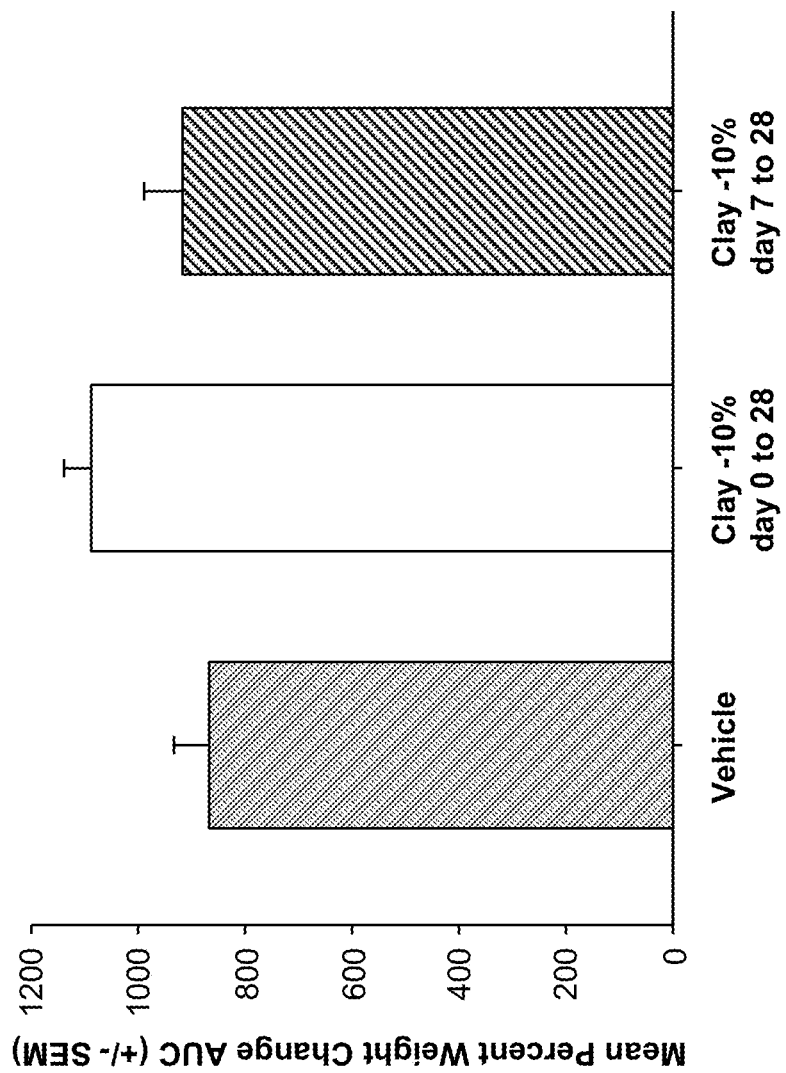

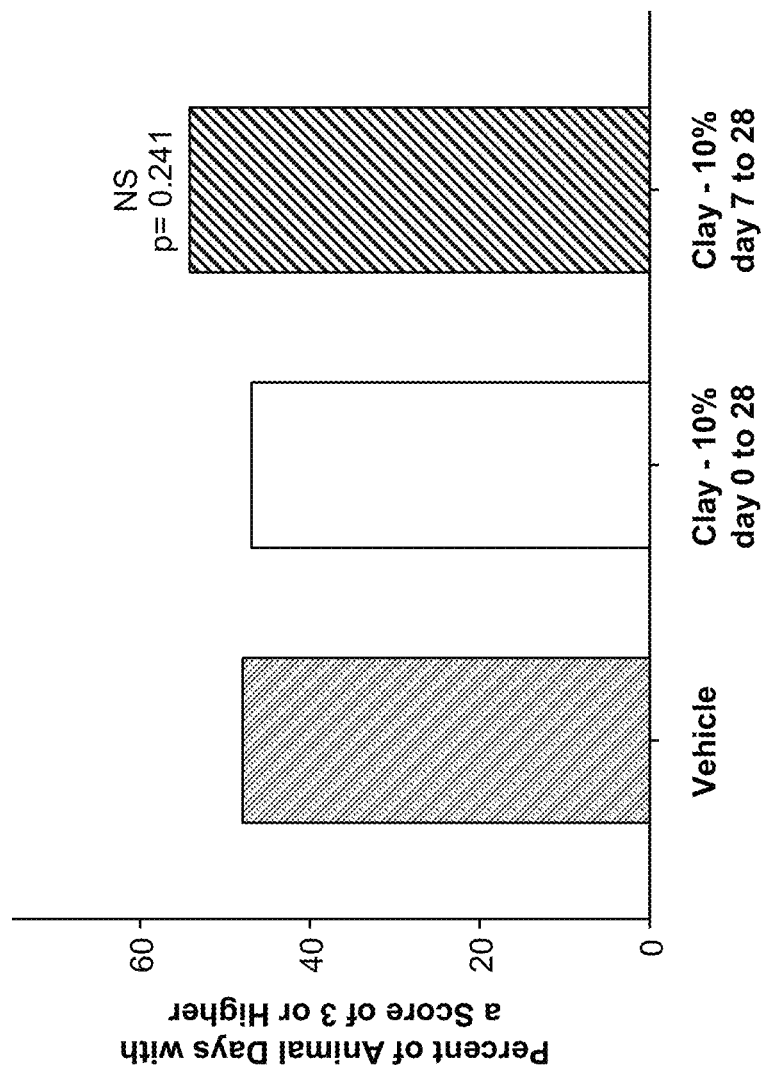

METHODS AND COMPOSITIONS FOR TREATING MUCOSITIS

CROSS-REFERENCE TO RELATED APPLICATIONS

The present application claims the benefit of priority to U.S. Provisional Patent Application No. 61/549,574, filed Oct. 20, 2011, which is incorporated herein by reference in its entirety.

TECHNICAL FIELD

The present disclosure relates to methods and compositions for preventing, treating, ameliorating and/or reducing the severity of mucositis. More particularly, the disclosure relates to methods for preventing, treating, ameliorating and/or reducing the severity of mucositis by providing a composition comprising a clay, and in one embodiment, a calcium-based clay that has no appreciable swelling in water.

BACKGROUND

Mucositis is a condition characterized by swelling, irritation, and discomfort of mucosal linings such as those of the alimentary and gastrointestinal tract, including oral and oral-pharyngeal cavities, as well as nasal, optical, vaginal and rectal mucosa. Mucositis can result in mouth and throat sores, diarrhea, abdominal cramping and tenderness, and rectal ulcerations. As an inflammation of mucous membranes which often involves infection and/or ulceration, mucositis is a serious and often very painful disorder.

Mucositis often develops as a complication of chemo- or radiation therapy for cancer. The goal of radiation and chemotherapy in cancer treatment is to kill rapidly dividing cancer cells; unfortunately, other rapidly dividing cells are killed by the treatment as well, including epithelial cells of the mucous membranes lining regions such as the gastrointestinal tract, leading to mucositis. Chemotherapy drugs are also used in HIV/AIDS patients. Exposure to radiation and/or chemotherapeutics often results in significant disruption of cellular integrity in mucosal epithelium and the underlying connective tissue, leading to inflammation, infection and/or ulceration at mucosal sites such as, for example, in the mouth, throat and other portions of the GI tract.

Mucositis adversely impacts the quality of life of cancer patients in several ways. Patients may experience intense pain, nausea and gastro-enteritis. The mouth and throat sores of mucositis can cause significant pain and make it difficult to eat, drink, and even take oral medication. In general, symptoms of mucositis appear within five to ten days after the start of cancer treatment and can last several weeks after cessation of treatment. The incidence of mucositis, as well as its severity, depends on factors such as the type and duration of the cancer treatment. Mucositis occurs, for example, in virtually all patients who are treated by irradiation of the head and neck. It is also highly prevalent in patients treated with high dose chemotherapy and/or irradiation for the purpose of myeloablation, in preparation for stem cell or bone marrow transplantation. The severity of mucositis can limit subsequent doses of chemotherapy or radiation. Efforts to counter the discomforts of mucositis can lead to disruptions in cancer treatment, alterations in treatment dosages, or shifting to different modes of treatment. Severe mucositis can also lead to the need for parenteral nutrition or hospitalization for several weeks (or more) of intravenous feeding as a result of the mouth ulcers, cramps, extreme pain, gut denuding and severe diarrhea. Thus, the development of effective approaches to preventing and treating mucositis is therefore important for improving the care of cancer patients.

Oral mucositis (OM) is an example of a specific type of mucositis, and is an acute, painful, costly and sometimes debilitating complication of some cancer therapies. Oral mucositis is prevalent in patient populations with head and neck malignancies being treated with radiation therapy. The oral cavity is lined with mucosal epithelium, and exposure to radiation and/or chemotherapeutics results in the disruption of cellular integrity leading to the development of ulcerative lesions. The mucositis can be mild requiring little intervention, to severe (hypovolemia, electrolyte abnormalities, and malnutrition) that may result in fatal complications—and this condition affects a significant fraction of cancer patients world-wide.

Oral mucositis usually occurs after the second week of radiation therapy, with severe symptoms usually resolving within six weeks following completion of therapy. In severe cases, Oral mucositis can be extremely painful, preventing the patient from eating, and requiring hospitalization for hydration, narcotics for pain, and/or total parenteral nutrition. Pain resulting from mucositis is so severe that it is often cited by cancer patients as the primary reason for discontinuing treatment. Patients suffering from oral mucositis have reported feeling as if they were drinking scalding hot water and scraping the inside of their mouth with coarse sand paper followed by running their tongue over a cheese grater. Oral mucositis can also be life-threatening because oral ulcerations can permit the entry of bacteria into the bloodstream, which can lead to fatality in the case of sepsis in a patient already immune-compromised by treatment for cancer. Oral mucositis is therefore a significant risk factor for life-threatening systemic infection; the risk of systemic infection is exacerbated by concomitant neutropenia, which is another complication associated with chemotherapy. Patients with oral mucositis and neutropenia have a relative risk for a life-threatening systemic infection that is at least four times greater than that of individuals without oral mucositis.

The onset of oral mucositis usually involves a four-phase process: the primary phase is inflammatory/vascular in nature, marked by cytokine release from the epithelium brought on by damage caused by radiation and/or chemotherapy. The second phase, referred to as the epithelial phase, is signaled by atrophy and ulceration of the mucosal epithelium. The third phase is defined as the ulcerative/bacterial phase represented by ulcerative lesions that are prone to bacterial infection further compromising the patients' immune system. These painful lesions often limit a patient's ability to eat and drink and in some cases require hospitalization. The presence of these lesions can also interrupt scheduled chemotherapy and/or radiation treatments. The last phase, the healing phase, is characterized by a proliferation and differentiation of epithelium as well as bacterial control.

Virtually all patients treated for tumors of the head and neck, patients receiving radiation along the GI tract, and around 40% of those subjected to radiation therapy and/or chemotherapy for tumors in other locations (leukemias or lymphomas) develop mucositis affecting the oral cavity and the rectum (Minerva *Stomatol.* 2002: 51:173-86). For example, esophagitis (or esophageal mucositis) is a major complication of chemo- and radiation therapy in patients with non-small cell lung cancer that produces significant morbidity and results in treatment interruptions. Mucositis also affects 76-100 percent of patients receiving higher doses of chemotherapy for bone marrow transplantation. Mucositis afflicts over 400,000 patients a year in the US, and the incidence is growing as the need for radiation and chemotherapy treatments grows.

Mucositis patients are highly susceptible to infection, as a breach in the otherwise protective linings of the oral mucosa and gastrointestinal tract can have serious consequences. The alimentary canal and GI tract are colonized by a vast array of microorganisms, and mucosal lesions can serve as portals of entry for endogenous microorganisms, becoming sites of secondary infection. Although not entirely supported by controlled clinical trials, allopurinol mouthwash and vitamin E have been cited as agents that may decrease the severity of oral mucositis. Prophylaxis against fungal infections is commonly employed in an effort to treat oral mucositis and includes use of topical antifungal agents such as nystatin-containing mouthwashes and clotrimazole troches. Although topical antifungal prophylaxis and treatment may clear superficial oropharyngeal infections, topical agents tend not to be well absorbed and have not been demonstrated to be effective against more deeply invasive fungal infections, which typically involve the esophagus and lower gastrointestinal tract. For this reason, systemic agents are indicated for treating all except superficial fungal infections in the oral cavity.

Treatment of mucositis is a significant unmet medical need. Current treatment strategies are primarily palliative, such as cryotherapy (ice chips) to reduce pain and inflammation, and analgesics to manage pain, including mucosal coating mixtures that may contain topical anaesthetics and antibiotics to control the opportunistic infection. These treatments provide little benefit, and do not speed healing or decrease severity of mucositis. Agents capable of reducing mucous absorption of the chemotherapy drugs (for example cryotherapy, allopurinol or pilocarpine etc.) have been used, as well as agents which reduce the changes in epithelial proliferation (for example beta-carotene, glutamine or silver nitrate etc.) or anti-inflammatory and antimicrobial agents (for example, mesalazine and/or chlorhexidine). Agents which protect the mucosa (for example, sodium bicarbonate), anaesthetic or analgesic agents (for example, lidocaine, morphine and the derivatives thereof etc.), and agents which accelerate the healing process (for example, vitamin E, tretinoin, laser therapy etc.) or special diets and/or specific oral hygiene regimens have also been employed. The only currently approved therapeutic for mucositis is Kepivance™ which is the known mitogenic protein keratinocyte growth factor (KGF) that must be administered intravenously. Kepivance™ is approved for a single indication which comprises only 4% of the total mucositis population, i.e., treatment of mucositis resulting from pre-conditioning regimens (chemotherapy and radiation) in stem-cell transplant patients. Other compounds have been evaluated for use as a prophylaxis and treatment of oral mucositis. Analgesics such as lidocaine mouthwashes are effective for short periods of time but within hours the pain and discomfort usually returns.

Given that a large number of patients suffer mucositis annually and patients undergoing cancer therapy often receive multiple cycles of chemotherapy and/or radiation therapy, there is a significant need for improved treatment of mucositis. The present disclosure is directed to this need.

BRIEF SUMMARY

The following aspects and embodiments thereof described and illustrated below are meant to be exemplary and illustrative, not limiting in scope.

In one aspect, a method of treating a mucositis is provided, wherein the mucositis affects a cavity selected from the group consisting of the mouth, esophagus, nose, orbit, vagina and rectum, said method comprising the method comprising administering to a subject a therapeutically effective amount of a composition comprising a clay.

In another aspect, a method to reduce or delay the onset of mucositis is provided, the method comprising administering to a subject a therapeutically effective amount of a composition comprising a clay.

In yet another aspect, a method for preventing mucositis in a subject is provided, the method comprising administering to a subject a therapeutically effective amount of a composition comprising a clay.

In still another aspect, a method for reducing severity of mucositis in a subject is provided, the method comprising administering to a subject a therapeutically effective amount of a composition comprising a clay, comprising:

In one embodiment, the clay for use in any of the methods described herein is a low-swelling or a non-swelling, calcium species of clay.

In one embodiment, the clay is a smectite clay.

In another embodiment, the clay is a calcium montmorillonite clay. In one embodiment, the montmorillonite clay comprises a majority of particles with a dry state fractionation size of between about 50-200 µm. In another embodiment, the montmorillonite clay comprises a majority of particles with a wet state fractionation size of less than 2 µm. In a specific embodiment, the montmorillonite clay is non-swelling and a calcium species as evidenced by a shrink/swell potential (SV) of less than 1.5 COLE index value. In yet another embodiment, the montmorillonite clay exhibits an extractable bases value for calcium of greater than 90 mEq/100 g clay, when extracted using ammonium acetate, or a value for calcium of between 6-12 mEq/100 g clay/L when extracted with deionized water.

In yet another embodiment, the clay has a uniform particle size that is achieved by sieving or air classification of the clay.

The method, in one embodiment, is provided to a subject with oral mucositis. In other embodiments, the subject is one at risk of developing oral mucositis.

The method, in another embodiment, is provided to a subject with gastrointestinal mucositis.

The method, in another embodiment, is provided to a subject with cancer.

In other embodiments, the method is provided to a subject undergoing or planning to undergo chemotherapy.

In still other embodiments, the method is provided prior to or concurrent with initiation of radiation therapy in the cancer subject.

In yet other embodiments, the method comprises administering after radiation therapy. Alternatively, the method can comprise administering for the duration of radiation therapy.

In other embodiments, the method comprises administering the clay composition more than once daily.

In one embodiment, the composition is administered orally as a fluid comprising the clay. The fluid can be, for example, a solution, a suspension, a paste, or a gel. In some embodiments, the fluid is held in the mouth for a recommended period of time. In other embodiments, the fluid is swallowed or discharged from the mouth after a recommended period of time.

In other embodiments, the clay-containing composition further comprises a polymer.

In one embodiment, the polymer is a bioadhesive polymer.

In still other embodiments, the clay containing composition comprises a solid dosage form that disintegrates in an aqueous medium. In one embodiment, the aqueous medium is a body fluid.

In other embodiments, the subject receiving the treatment method is concurrently treated with at least one therapeutic agent. In exemplary embodiments, the therapeutic agent is a pain reliever or a chemotherapeutic; an anti-inflammatory or antibiotic. In one embodiment, the pain reliever is a topical anaesthetic selected from the group consisting of fentanyl, hexylresorinol, dyclonine hydrochloride, asbenzocaine and phenol. In a preferred embodiment, the pain reliever is fentanyl.

In one embodiment, the composition for administration is provided in form such that prior to administering, the clay is contacted with a fluid to form a composition suitable for oral administration.

Further, the present disclosure includes compositions including the compounds described herein, formulated for administration for reducing the severity of mucositis as described herein. As is described in detail below, these compositions can include the compounds in formulations such as gels for topical administration, rinses, tablets, capsules, chewing gum, lozenges, creams, ointments, enemas, suppositories, or patches. In some embodiments, the compositions are administered topically, to a mucous membrane. In some embodiments, the composition is administered orally, for swallowing (ingesting) by the subject so that the composition reaches the esophagus and gastrointestinal tract.

In other aspects, the present disclosure provides methods for treating, ameliorating or preventing mucositis comprising administering to a subject a therapeutically effective amount of a composition comprising a clay. Patients to be treated according to the disclosed methods and compositions include those who have mucositis (e.g., oral or gastrointestinal mucositis). In addition, patients who do not have, but are at risk of developing, mucositis (e.g., oral or gastrointestinal mucositis) can be treated according to the present disclosure. In the latter group of patients, the treatment can inhibit, delay or prevent the development of mucositis. In some embodiments, the patient to be treated is a subject having cancer. In some embodiments, the subject to be treated is suffering from mucositis or is at risk of developing mucositis. In some embodiments, the mucositis to be treated, ameliorated or prevented is oral mucositis. In some embodiments, the mucositis to be treated, ameliorated or prevented is gastrointestinal mucositis. In one embodiment, the patient to be treated has not been and is not currently receiving a vitamin D therapy.

In certain embodiments, the subject has received or will be receiving radiation therapy or chemotherapy. In certain embodiments, the mucositis is caused or is likely to result from radiation-induced toxicity in non-malignant tissue. In other embodiments, the mucositis is caused or is likely to result from chemical-induced toxicity in non-malignant tissue. In one embodiment, the chemical-induced toxicity is not caused by docetaxel.

In one embodiment, the subject to be treated is a bone marrow transplantation patient. In another embodiment, the subject to be treated is a cancer patient. The subject may have any type of cancer. In certain embodiments, the subject has leukemia, lymphoma, rectal or colorectal cancer, breast cancer, prostate cancer, androgen-dependent prostate cancer, lung cancer, mesothelioma, head and neck cancer, esophageal cancer, gastric cancer, pancreatic cancer, gastrointestinal cancer, renal cell cancer, testicular cancer, germ cell cancer, glioma or any other primary or solid tumor. In one embodiment, the subject does not have androgen-independent prostate cancer.

Examples of treatments that may cause or place a patient at risk of developing mucositis (e.g., oral or gastrointestinal mucositis) are radiation therapy and/or chemotherapy, as described further elsewhere herein or in the background section. Patients that can be treated according to the present disclosure thus include, for example, cancer patients, HIV/AIDS patients, as well as patients that have recently been, will shortly be, or are currently subject to treatment with head or neck irradiation, or stem cell or bone marrow transplantation.

According to the disclosed methods, compositions used herein can be administered to a patient prior to, concurrently with, or after a treatment that has induced or places the patient at risk of developing mucositis (e.g., oral or gastrointestinal mucositis), or a combination of these approaches can be used. In an example, the composition is administered at the same time as, within 1-4 hours of, or on the same day as the treatment, and then for 1-3 (e.g., 1-2) days thereafter (e.g., 1-2 times per day). Other examples of treatment regimens are provided below.

The compositions can be administered to patients by any acceptable manner known in the art, including topically (e.g., by gel, rinse, lozenge, cream, ointment, or patch), orally (e.g., by tablet, capsule, lozenge, cream, ointment, or patch), rectally (e.g., by suppository, ointment, or enema), nasally, optically or vaginally (e.g., by cream, ointment, gel, or suppository). Also, treatment according to the present disclosure can be carried out in combination with other approaches to treating mucositis, including antimicrobial and palliative treatments, as is discussed further below.

In some embodiments, the subject is concurrently treated with at least one therapeutic agent. In some embodiments, the therapeutic is a pain reliever or a chemotherapeutic. In some embodiments, the therapeutic agent is an anti-inflammatory or antibiotic. In some embodiments, the pain reliever is a topical anaesthetic selected from, but not limited to, the group consisting of fentanyl, hexylresorinol, dyclonine hydrochloride, asbenzocaine and phenol. In some embodiments, the administering comprises administering to a subject undergoing or planning to undergo chemotherapy. In some embodiments, the administering is prior to or concurrent with initiation of radiation therapy in the cancer subject. In some embodiments, the administering is after radiation therapy. In some embodiments, the administering continues for the duration of radiation therapy. In some embodiments, the administering continues for longer than the duration of radiation therapy. In some embodiments, the administering continues for a time shorter than the duration of radiation therapy. In some embodiments, the administering comprises administering more than once daily. In some embodiments, the administering comprises administering once daily.

In some embodiments, the composition used in the method does not include vitamin D. In some embodiments, the therapeutic agent is not vitamin D. In some embodiments, the patient is not being or has not been treated with vitamin D.

In addition to the exemplary aspects and embodiments described above, further aspects and embodiments will become apparent by reference to the drawings and by study of the following descriptions.

BRIEF DESCRIPTION OF THE FIGURES

FIG. 1B is a bar graph showing the area under the curve (AUC) calculated for the percentage weight change in the animals of FIG. 1A;

FIG. 2B is a bar graph showing the percent of animals days with a mucositis score of 3 or higher, where the total number of days in which an animal in one of the three treatment groups exhibited score of 3 or higher was summed and expressed as a percentage of the total number of days scored. Statistical significance was evaluated using the Chi-squared test.

Figure 1A:
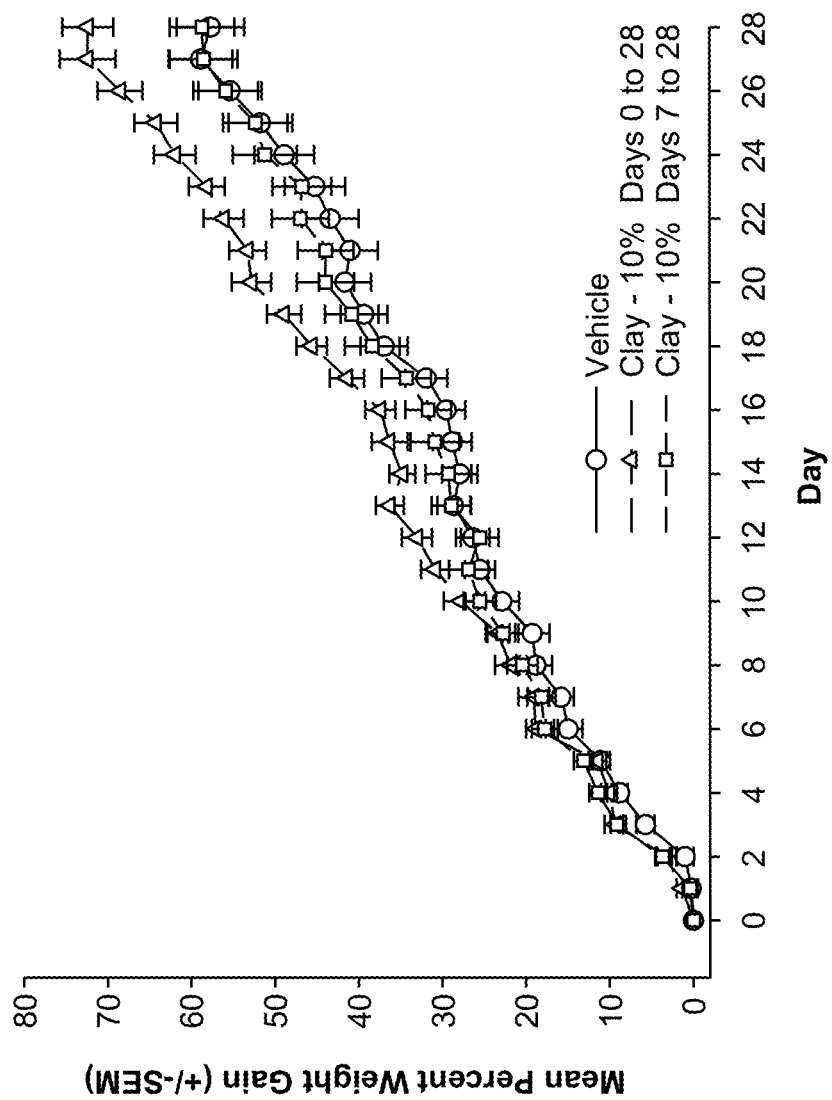
FIG. 1A shows the mean percentage weight change as a function of day in animals with induced oral mucositis and left untreated (circles) or treated three times daily with a clay composition for two different time periods, from study day 0-29 (triangles) or from study day 7-28 (squares)

Various aspects now will be described more fully hereinafter. Such aspects may, however, take many different forms and should not be construed as limited to those embodiments explicitly set forth herein. Rather, these embodiments are provided so that this disclosure will be thorough and complete, and will fully convey its scope to those skilled in the art.

DETAILED DESCRIPTION

I. Definitions

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

As used herein, "mucositis" refers to the inflammation ulceration of the mucous membranes, more specifically of mucosal epithelium, such as that in the alimentary tract including but not limited to the inner lining of the mouth, gastrointestinal tract, pharyngeal passages, nasal passages, vagina, optical cavity, bladder and urethra, and the mucosal epithelium of the gastrointestinal tract from the mouth to anus.

The term "oral mucositis" intends inflammation and/or destruction of the mucosal epithelium lining of the mouth cavity, including the cheeks, gums, tongue, lips, the roof or floor of the mouth.

The term "gastrointestinal mucositis" intends inflammation and/or destruction of the mucosal lining of all or a portion of the gastrointestinal tract, including the stomach, duodenum, jejunum, and/or colon, caecum and/or rectum, and excluding the mouth cavity.

"Stomatitis" refers to mucositis affecting any oral, pharyngeal and/or laryngeal epithelial surface, and includes an inflammation of the mucous lining of any or all of the cheeks, gums, tongue, lips, throat or the roof or floor of the mouth, or ulceration of these mucosal surface.

Esophagitis" refers to mucositis affecting the esophagus.

As used herein, the phrase "therapeutically effective amount" refers to an amount which provides a therapeutic benefit, wherein benefits can include, the prevention, treatment or amelioration of mucositis.

II. Methods of Treatment

In a first aspect, a method for preventing, treating, ameliorating and/or reducing the severity of mucositis is provided. As will be illustrated by the studies discussed herein, administration of a composition comprising a clay is effective in treating, slowing the progression of, reducing the severity of, and preventing mucositis. These studies are described in Section A. In Section B, clays and formulations comprising a clay for use in the treatment methods are described, and in Section C, treatment regimens in general and for particular patient populations are disclosed.

A. Treatment of Mucositis

Studies were conducted in support of the claimed methods to demonstrate the efficacy of a composition comprising a clay to prevent mucositis, treat mucositis, ameliorate the severity of mucositis and/or reduce the severity of mucositis. As described in Example 1, an acute radiation model was used wherein mucositis was induced in the buccal pouch of hamsters. In the study, an acute radiation dose of 40 Gy was administered to each animal. Clinically significant mucositis was observed on days 12 through 28.

A composition comprising clay was given topically to the left cheek pouch three times daily either from Day 0 to Day 28 (Group 2) or from Day 7 to 28 (Group 3). As a control, animals in Group I received a saline vehicle three times daily at the same dose volume as the clay compositions. The clay selected for use in the study was a calcium-based aluminosilicate clay, which is essentially non-swelling in aqueous fluids. The clay is discussed in more detail hereinbelow.

Mucositis in the left cheek pouch for the treated and control animals was evaluated clinically starting on Day 6, and continuing on alternate days until Day 28. The weight and general health of the animals were evaluated daily. Beginning on day 6 and continuing on alternate days for the duration of the study, oral mucositis was scored using a standard six point scale, set forth in Example 2 below. The number of days of ulcerative mucositis was evaluated using a chi-squared test of mucositis scores of 3 or higher, and the individual daily group scores were assessed with a rank sum test.

The mean daily percent weight change of the test animals is presented in FIG. 1A. The saline vehicle-treated control hamsters (circles) gained an average of 51.9% of their starting weight during the study. Hamsters in the group treated with 10% clay from Day 0 to 28 (triangles) gained an average of 59.5% of their starting weights during the study. Hamsters in the group treated with 10% clay from Day 7 to 28 (squares) gained an average of 62.7% their starting weights during the course of the study. It is interesting to note that the 10% clay from Day 0 to 28 treatment group showed no difference in weight gain from the other groups until Day 10 when the mucositis begins to becomes significant. After Day 10 the Day to 28 clay group gained substantially more weight than either the vehicle control group of the group treated with clay from Day 7 to 28.

The statistical significance of these differences was evaluated by calculating the area-under-the-curve (AUC) using the trapezoidal rule transformation for the weight gain of each animal, and then comparing the different treatment groups using a One-Way ANOVA test. The results of this analysis indicated that there were no significant differences between any of the treatment groups (p=0.056). These data are shown in FIG. 1B.

The grade of mucositis was scored, beginning on day 6, and for every second day thereafter, through and including day 28. The effect on mucositis of each drug treatment compared to placebo was assessed. On each evaluation day, the number of animals with a blinded mucositis score of ≥3 in each drug treatment group was compared to the control group. Differences were compared on a cumulative basis and statistical significance was determined by chi-square analysis. Efficacy in this analysis is defined by a significant reduction in the number of days that a group of animals had ulcerations (scores ≥3) when compared to the control group.

Figure 2A:
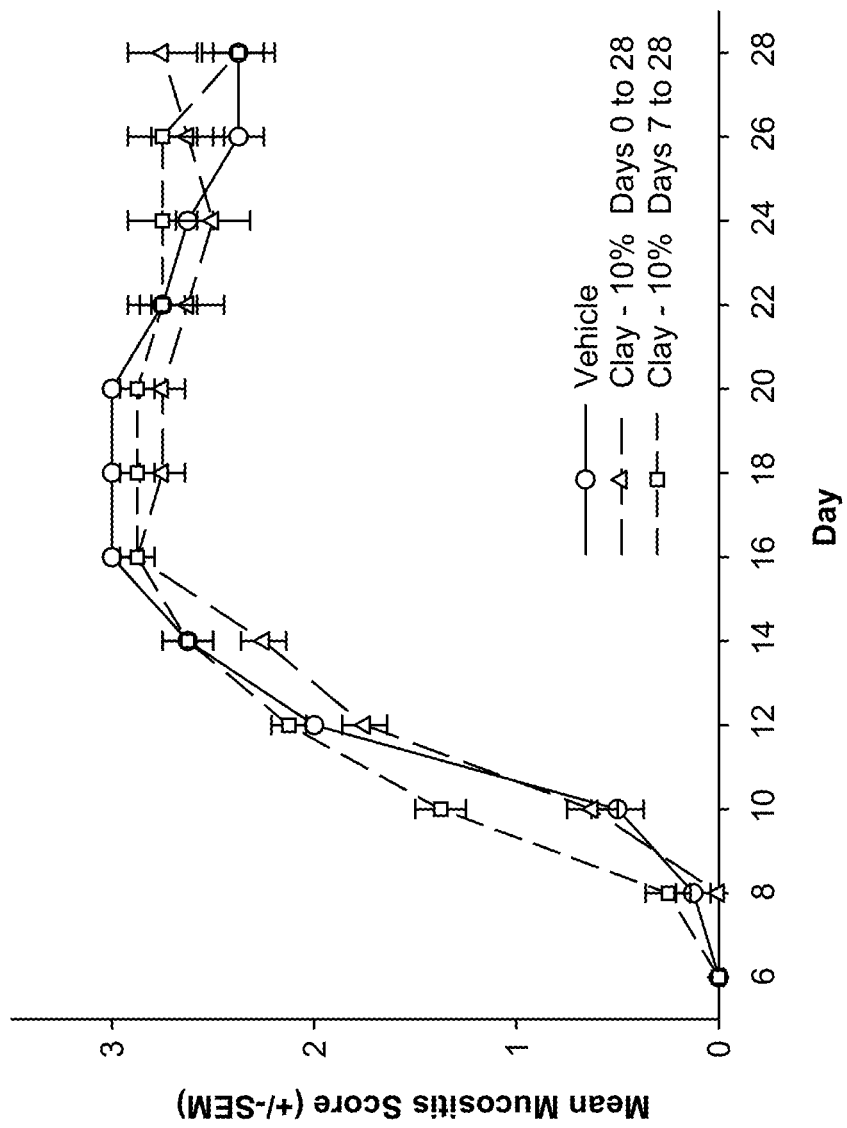
FIG. 2A is a graph of the mean mucositis score as a function of day, for animals with induced oral mucositis and untreated (circles) or treated three times daily with a clay composition for two different time periods, from study day 0-29 (triangles) or from study day 7-28 (squares)

The results of this analysis are shown in Table 1 and FIGS. 2A-2B.

TABLE 1

$\chi^2$ analysis of the total number of days the animals in each group spent with a score of three or more. This statistic is a measure of severity of ulceration, a clinically important outcome.

| Treatment Group | Days ≥ 3 | Days < 3 | Total Animal Days | % Days ≥ 3 | Chi Sq vs. Control | P Value |
|---|---|---|---|---|---|---|
| 1 (Vehicle Control) | 92 | 100 | 192 | 47.92% | — | — |
| 2 (10% clay, Day 0 to 28) | 90 | 102 | 192 | 46.88% | 0.0104 | p = 0.919 |
| 3 (10% clay, Day 7 to 28) | 104 | 88 | 192 | 54.17% | 1.261 | p = 0.261 |

In the vehicle control group, the percentage of animal days with a score of 3 or higher was 47.9%. In the group treated with 10% clay from Day 0 to 28, the percentage of animal days with a score of 3 or higher was slightly reduced, to 46.9%. In the group treated with 10% clay from Day 7 to 28, the percentage of animal days with a score of 3 or higher was increased, up to 54.2%.

An analysis of the severity of mucositis was performed using the Mann-Whitney rank sum analysis to compare the scores for each treatment group to the controls on each day of the analysis. In this analysis, 2 days of significant reduction in the mucositis score are generally required before it is regarded as meaningful. The p values for each calculation are shown. The results of this analysis are shown in Table 2. Significant improvements are shown underlined and in bold, while significant worsening of disease is shown underlined in italicsandunderlined.

The group treated with 10% clay from Day 0 to 28 showed significant reductions in mucositis scores relative to vehicle controls on four separate days of the study (Days 12, 14, 18, and 20) while those where treatment started later, on day 7, did not exhibit any days of significant improvement. Interestingly, there was a trend for significant worsening of mucositis as the disease begins to resolve between Days 26 and 28 in those animals treated with clay. This suggests that dose scheduling studies may play a role in determining the most effective timing of clay treatment.

Treatment of the animals with a clay-containing composition was effective in reducing the severity of oral mucositis when dosed from Day 0 to 28. Importantly, the clay treatment resulted in a substantial reduction in percent of animals with ulcerative mucositis during peak disease from Days 14 to 20.

Treatment with 10% clay from Day 0 to 28 significantly reduced the daily mucositis scores on four of the twelve days evaluated when compared to vehicle control. Treatment with 10% clay from Day 0 to 28 reduced the percent of animals with ulceration compared to vehicle control by 37.5% on Day 14, by 12.5% on Day 16, and by 25% on Days 18 and 20.

Mucositis typically progresses in five phases. Phase 1, "the initial phase," includes: DNA strand breaks, and reactive oxygen species generation. Phase 2, "the primary damage response phase" includes: activation of NFκB and p53 pathway; NFκB up-regulation of genes that may exert an effect on mucosal toxicity, including apoptosis-regulating genes of the BCL2 family; up-regulation of c-Jun and c-Jun amino-terminal kinase, which in turn up-regulates NRF2; and production of proinflammatory cytokines, TNF-alpha, IL-1β, IL-6, the presence of which may cause damage to epithelium via reduced oxygenation and basal cell death, endothelium, and connective tissue; radiation and some cytotoxic agents also cause apoptosis via hydrolyzation of sphingomyelin (a cell-membrane lipid), a process that increases ceramide levels and results in cell apoptosis; fibroblasts in the submucosa may be damaged by radiation or chemotherapy, either directly or via stimulation of metalloproteinases. Phase 3, "the signal amplification phase," includes: a range of proteins that accumulate and target the submucosa, causing tissue damage and initiating a positive feedback loop, amplifying the primary damage caused by the radiation or chemotherapy. For example, a pathway that results in cell death is activated by TNF-alpha, which in turn activates NFκB and initiates mitogen-activated protein kinase (MAPK) signaling, in turn activating JNK (a member of the MAP kinase family), in turn regulating the activity of AP 1. Cell death caused by this pathway occurs in the submucosa as well as the epithelium. TNF-alpha and IL-1 beta. both induce matrix metalloproteinase activation. Phase 4, "the ulcerative phase," may include: functional trauma caused lesions (e.g., with respect to oral mucositis, the lesions

TABLE 2

A Comparison of Daily Mucositis Scores.

| Group Comparison | Treatment Day | | | | | | | | | | | |
|---|---|---|---|---|---|---|---|---|---|---|---|---|
| | 6 | 8 | 10 | 12 | 14 | 16 | 18 | 20 | 22 | 24 | 26 | 28 |
| Group 1 vs. Group 2 (vehicle vs. clay-Day 0 to 28) | 1.000 | 0.164 | 0.497 | 0.038 | 0.037 | 0.164 | 0.038 | 0.038 | 0.862 | 0.808 | 0.107 | <u>0.018</u> |
| Group 1 vs. Group 3 (vehicle vs. clay-Day 7 to 28) | 1.000 | 0.388 | <u><0.001</u> | 0.164 | 0.982 | 0.164 | 0.164 | 0.164 | 0.524 | 0.204 | <u>0.018</u> | 0.816 | appear in the mouth); excessive bacterial colonization of lesions, (e.g., with respect to oral mucositis, the bacterial colonization of lesions may be exacerbated by reduced salivary levels and poor oral hygiene as often happens in neutropenic patients); endotoxin released from gram-negative organisms and cell wall products from gram-positive bacteria may then interact with tissue macrophages to trigger release of further IL-1 and TNF-alpha, exacerbating mucosal damage. Secondary infections that result include fungal infections, viral infections and bacterial infections. Phase 5, "the healing phase," includes cell proliferation and differentiation returns to normal; bone marrow recovery results in increased numbers of white cells and control of local infection.

In another study conducted in support of the claimed methods, the binding of cytokines to an exemplary clay for treatment of mucositis, calcium aluminosilicate clay, was investigated. In this study, a fixed concentration of cytokine was exposed to varying concentrations of clay for 15 minutes at room temperature. The samples were stirred occasionally and then centrifuged. The concentration of protein was determined using a sandwich immunoassay kit (R&D Systems, Minneapolis, Minn.) and compared to that measured in a sample without clay. Results are shown in Table 3.

TABLE 3

| Material | Concentration (pg/mL) | Clay Concentration (mg/mL) | | | |
|---|---|---|---|---|---|
| | | 0.01 | 0.1 | 1.0 | 10.0 |
| | | Percent of Cytokine Bound by Clay | | | |
| IL-1β | 750 | 40 | 52 | 71 | 80 |
| IL-6 | 750 | 35 | 41 | 45 | 89 |
| IL-8 | 200 | 0 | 29 | 43 | ND |
| TNF-α | 750 | 5 | 61 | 90 | 99 |

The data in Table 3 shows that pro-inflammatory cytokines such as TNF-alpha are readily bound by the clay. At a concentration of 1 mg/mL clay, 90% of the TNF-alpha was removed from solution presumably by direct binding to the clay. Binding IL-1 beta by the clay was moderate while binding of IL-6 and IL-8 was weak. The unique ability of the clay to bind TNF-alpha was further investigated, as blocking the action of TNF can be beneficial in reducing the inflammation in mucositis and in other diseases. The study is described in Example 3, and the data is presented in FIGS. 3A-3B. The data presented in the two graphs demonstrates the removal of TNF-alpha from a stock solution of this pro-inflammatory protein. Even concentrations of the calcium aluminosilicate clay as low as 0.5 mg/ml removed greater than 90% of all TNF-α from solution. The study demonstrates the capacity to bind and remove from solution important inflammatory components such as tumor necrosis factor and, also illustrates the small amount of clay needed to achieve a benefit. The later type of information is of direct relevance in determining appropriate doses for clay compositions.

Accordingly, in one embodiment a composition comprising a clay to prevent mucositis, treat mucositis, ameliorate the severity of mucositis and/or reduce the severity of mucositis is provided to a subject in need. The ability of the clay to alter the pro-inflammatory environment in the tissue area is demonstrated by the data, and the efficacy of the clay to prevent and ameliorate mucositis is evident from the animal studies. In a first specific embodiment, a clay is administered to a subject at risk of developing or presenting with a mucositis other than oral mucositis. In a second specific embodiment, a clay is administered to a subject at risk of developing or presenting with a mucositis selected from esophageal mucositis, gastrointestinal mucositis (wherein gastrointestinal intends that part of the gastrointestinal tract after the esophageous and before the rectum; that is the stomach, small intestine (duodenum, jejunum, and ileum) and large intestine (cecum, vermiform appendix, colon, and rectum)), rectal mucositis, anal mucositis, nasal mucositis and vaginal mucositis.

B. Clay and Formulations Comprising Clay

The methods of treatment comprise providing to a patient, for administration by a suitable route depending on the location in the body of the mucosal tissue experiencing mucositis, the extent of tissue damage and condition of the patient, a composition comprising the clay.

B1. Clay

Clays are a distinguished from other fine-grained earth deposits, and are grouped distinct classes such as kaolinites, illites, smectites. Clays based on silicates form a large class, where the basic structural unit for silicate clays is a SiO4 tetrahedron in which $Sr^{4+}$ is located at the center and four $O^{2-}$ are positioned at the apices. The tetrahedral structures can be linked together by sharing four $O^{2-}$ ions and together can form a variety of more complex structures including rings (cyclosilicates), chains (inosilicates), sheets (phyllosilicates) and three dimensional arrangements (tectosilicates). Tetrahedra, e.g., $SiO_4$ and octahedral, e.g., $Al_2O_3$ are common structural components in many mineral structures.

In one embodiment, the clay for use in the methods described herein is a phyllosilicate clay. Phyllosilicate clays contain both tetrahedral and octahedral sheets, and are further categorized according to composition and packing arrangement. In some embodiments, the clay material is a phyllosilicate selected from the group consisting of kanemite, kenyaite, magadiite and makatite. In some embodiments, the phyllosilicate is selected from the group consisting of allophane (hydrated aluminum silicate); apophyllite (hydrated potassium sodium calcium silicate hydroxide fluoride); bannisterite (hydrated potassium calcium manganese iron zinc aluminum silicate hydroxide); carletonite (hydrated potassium sodium calcium silicate carbonate hydroxide fluoride); cavansite (hydrated calcium vanadate silicate); chrysocolla (hydrated copper aluminum hydrogen silicate hydroxide); clay minerals (described in detail below); delhayelite (hydrated sodium potassium calcium aluminum silicate chloride fluoride sulfate); elpidite (hydrated sodium zirconium silicate); fedorite (hydrated potassium sodium calcium silicate hydroxide fluoride); franklinfurnaceite (calcium iron aluminum manganese zinc silicate hydroxide); franklinphilite (hydrated potassium manganese aluminum silicate); gonyerite (manganese magnesium iron silicate hydroxide); gyrolite (hydrated calcium silicate hydroxide); kanemite; kenyaite; leucosphenite (hydrated barium sodium titanium boro-silicate); magadiite; makatite; micas such as biotite (potassium iron magnesium aluminum silicate hydroxide fluoride), lepidolite (potassium lithium aluminum silicate hydroxide fluoride), muscovite (potassium aluminum silicate hydroxide fluoride), paragonite (sodium aluminum silicate hydroxide), phlogopite (potassium magnesium aluminum silicate hydroxide fluoride) and zinnwaldite (potassium lithium aluminum silicate hydroxide fluoride); minehillite (hydrated potassium sodium calcium zinc aluminum silicate hydroxide); nordite (cerium lanthanum strontium calcium sodium manganese zinc magnesium silicate); octosilicate; pentagonite (hydrated calcium vanadate silicate); petalite (lithium aluminum silicate); prehnite (calcium aluminum silicate hydroxide); rhodesite (hydrated calcium sodium potassium silicate); sanbornite (barium silicate); serpentines such as antigorite (magnesium iron silicate hydroxide), clinochrysotile (magnesium silicate hydroxide), lizardite (magnesium silicate hydroxide), orthochrysotile (magnesium silicate hydroxide) and serpentine (iron magnesium silicate hydroxide); wickenburgite (hydrated lead calcium aluminum silicate); and zeophyllite (hydrated calcium silicate hydroxide fluoride).

In one embodiment, the clay is a dioctahedral smectite, calcium aluminosilicate clay. Calcium aluminosilicate clay is a 2:1 phyllosilicate clay containing sheets of 6-membered rights, and is a very pure calcium montmorillonite clay in the dioctahedryl smectite group. Its general chemical formula is $(Na, Ca)_{0.3}(Al, Mg)_2Si_4O_{10}(OH)_2n(H_2)$. This clay is a 'non-swelling' clay due to the fact it contains more calcium than sodium. As used herein, essentially "low-swelling" and essentially "non-swelling" clay species means that the particular clay species has minimal capacity for changes in volume due to shrinkage or swelling. One approach to measure swelling potential is given in the Soil USDA Technical Handbook, where a COLE index value is assigned to materials. A COLE index value >0.03 indicates that a material may have a small amount of smectite clay within its composition and show low shrink/swell potential. Sodium montmorillonite clays swell much more in aqueous fluids than calcium montmorillonte clays. In one embodiment, the clay for use in the methods described herein is a montmorillonite clay that is non-swelling and a calcium species, as evidenced by a shrink/swell potential (SV) of less than 1.5 COLE index value. An exemplary non-swelling calcium clay is described in U.S. Patent Application Publication No. 2008/0026079, which is incorporated by reference herein. In one embodiment, the clay used in the methods described herein is a clay other than the specific calcium aluminosilicate clay described in U.S. Patent Application Publication No. 2008/0026079. That is, the clay used in the methods described herein is not the clay referred to as calcium aluminosilicate anti-diarrheal, with a uniform particle of less than about 100 microns or less than about 80 microns.

Due to the presence on the surface of many functional groups, clays are able to interact with other components of the formulation. Negative charges on the clay particles are compensated by counterions, for example Na+, Ca++, Ag+, and so forth, or a combination thereof. Cation exchange capacity (CEC) is an intrinsic property defining the concentration of negatively charged sites on clay particles. Cation exchange capacity is a measure of exchangeable bases in the clay material, and provides an indication of the capacity of the clay to exchange/interact with other compounds. The cationic exchange capacity of clays can be measured using the method described in Grimshaw, The Chemistry and Physics of Clays, Interscience Publishers, Inc., pp. 264-265 (1971). A common method for determining CEC uses 1 M ammonium acetate ($NH_4OAc$) at pH 7 (neutral $NH_4OAc$) and is a standard method used for soil surveys by the Natural Resource Conservation Service. In one embodiment, the clay for use in the methods described herein exhibits an extractable bases value for calcium of greater than 90 mEq/100 g clay, when extracted using ammonium acetate, or a value for calcium of between 6-12 mEq/100 g clay/L when extracted with deionized water.

A skilled artisan will appreciate that clay can be sized by sieving or by air classification to achieve a desired average particle size. A skilled artisan in the relevant field will appreciate that any representative sample of clay will be polydisperse in size, yet the art provides several approaches for expressing the average size, or diameter, of particles in a population. For example, an average particle size, or uniform particle size, may in some embodiments intend that a representative sample of the clay when passed through a sieve of a certain mesh size retains a majority (greater than 50%) of the clay sample. Size fractionation (wet and dry) of a representative sample of a given clay can be done as follows. Wet state fractionation involves removal of cementing and flocculating materials in the sample using sodium acetate buffer (pH 5). Organic matter in the sample is removed using 30% hydrogen peroxide. The sample is then dispersed with 50 mL of pH 10 sodium carbonate solution. The sand fraction (>53 μm) is separated using a 53 μm sieve. The clay fraction (<2 μm) is separated from the silt fraction (2-53 μm) by centrifugation using pH 10 sodium carbonate as dispersant. Sand and silt weights are recorded after drying at 105° C. overnight. Clay suspension is flocculated with sodium chloride and then dialyzed until the electrical conductivity measurement were close to the values of deionized water (<2 μS/cm). Air dry fractionation of clay can be done using, for example, an Octagon 200 sieve shaker (Endecotts), and weight average particle size determined in accord with the manufacturer's instructions. For example, the percentage of particles with greater than 100 μm size, between 45-100 μm size, and less than 45 μm size is calculated. In one embodiment, the montmorillonite clay comprises a majority (i.e., 51%, based on weight percent) of particles with a dry state fractionation size of between about 50-200 μm. In other embodiments, the montmorillonite clay is comprised of a particles wherein at least 60%, 70%, 75% or 80% of the particles have a dry state fractionation size of between about 50-200 μm. In another embodiment, montmorillonite clay comprises a majority of particles with a wet state fractionation size of less than 2 μm. In another embodiment, the average particle size of the clay in a dry state is less than about 200 μm, or less than about 100 μm, or less than about 80 μm. In other embodiments, the average particle size of the clay is between 5-200 μm or between 5-50 μm. In one embodiment, the clay is a smectite clay, and more specifically a sodium calcium aluminosilicate with a particle size distribution of 5%+100 mesh (greater than 149 microns), 18%+200 mesh (greater than 74 microns) and 60%-325 mesh (smaller than 44 microns), sold under the tradename NovaSil Plus. In another embodiment, the particles in the clay have a dry state fractionation average size or average particle size of 100 microns or greater, alternatively of greater than about 100 μm, or alternatively of between about 100-500 microns, 100-300 microns, or 100-250 microns.

Suitable clay minerals include chlorites such as baileychlore (zinc iron aluminum magnesium silicate hydroxide), chamosite (iron magnesium aluminum silicate hydroxide oxide), the generallized mineral chlorite, clinochlore (a chromium variety kaemmererite) (iron magnesium aluminum silicate hydroxide), cookeite (lithium aluminum silicate hydroxide), nimite (nickel magnesium iron aluminum silicate hydroxide), pennantite (manganese aluminum silicate hydroxide), penninite (iron magnesium aluminum silicate hydroxide) and sudoite (magnesium aluminum iron silicate hydroxide); glauconite (potassium sodium iron aluminum magnesium silicate hydroxide); illite (hydrated potassium aluminum magnesium iron silicate hydroxide); kaolinite (aluminum silicate hydroxide); montmorillonite (hydrated sodium calcium aluminum magnesium silicate hydroxide); palygorskite (hydrated magnesium aluminum silicate hydroxide); pyrophyllite (aluminum silicate hydroxide); sauconite (hydrated sodium zinc aluminum silicate hydroxide); talc (magnesium silicate hydroxide); and vermiculite (hydrated magnesium iron aluminum silicate hydroxide). For example, palygorskite or attapulgite is a magnesium aluminium phyllosilicate with formula $(Mg,Al)_2Si_4O_{10}(OH).4(H_2O)$ which occurs in a type of clay soil common to the Southeastern United States. Attapulgite clays are a composite of smectite and palygorskite. Smectites are expanding lattice clays of which bentonite is a commonly known generic name for smectite clays. The palygorskite component is an acicular bristle-like crystalline form which does not swell or expand. Attapulgite forms gel structures in fresh and salt water by establishing a lattice structure of particles connected through hydrogen bonds. Attapulgite, unlike bentonite, will form gel structures in salt water and is used in special salt water drilling mud for drilling formations contaminated with salt. Palygorskite particles can be considered as charged particles with zones of + and − charges. It is the bonding of these alternating charges that allow them to form gel suspensions in salt and fresh water. Attapulgite clays found in the Meigs-Quincy district are bundles of palygorskite clay particles between 2 and 3 micrometers long and below 3 nanometers in diameter. The bundles are surrounded by a matrix of smectite clays which are slightly swellable. Dry process grades contain up to 25% non-attapulgite material in the form of carbonates and other mineral inclusions.

Kaolin is not as absorbent as most clays used medicinally and has a low shrink-swell capacity. Also, it has a low cation exchange capacity. This clay is also known as 'white cosmetic clay'. Clay, in the form of kaolin, is still a common ingredient in western medicines such as Rolaids and Maalox, as well as in cosmetics.

Swellable clay minerals are typically those that have alkali metals between their layers and can swell in polar solvents. These include lithium containing materials such as cookeite; sodium containing materials such as glauconite (which also contains potassium), montmorillonite and sauconite; and potassium containing materials such as illite.

In some instances, non-swellable materials are preferred over the swellable clay minerals.

It may be desirable to treat the phyllosilicate particles with an organic material to intercalate organic molecules between adjacent, planar silicate layers. For example, treatment can be with an organic material such as silane coupling agents; quaternary ammonium compounds; monomeric compounds having an electrostatic functionality selected from the group consisting of amines, amides and mixtures thereof; monomeric compounds having a functionality selected from the group consisting of hydroxyl, aromatic rings, carbonyl, carboxylic acid, polycarboxylic acid, aldehydes, ketones, amines, amides, ethers, esters and combinations thereof; and so forth.

B2. Formulations Comprising Clay

The clay is formulated with one or more pharmaceutical excipients to provide a composition for administration to a patient in need of treatment. Compositions contemplated for use in the methods are varied according to these, and other, factors, and exemplary formulations are now described.

In a first embodiment, a composition suitable for oral administration to a patient in need is contemplated. The composition comprises an amount of clay sufficient to achieve a desired therapeutic response when administered to the patient in accord with a defined protocol. Formulation of the clay into a form suitable for oral administration includes formulation to provided, for example, a liquid formulation such as a suspension, a solution, an elixir, or an emulsion, that can be used as a mouth rinse, spray or wash. Liquid formulations often are aqueous based and can include excipients to increase the viscosity to provide a coating on the mucosal tissue that lingers for a period of time after application. Mouthwash formulations are well-known to those skilled in the art and will often include excipients as, for example, pharmaceutical grades of mannitol, lactose, starch, magnesium stearate, sodium saccharine, cellulose, magnesium carbonate and/or the like. Exemplary formulations are discussed in detail, for example, in U.S. Pat. No. 6,387,352, U.S. Pat. No. 6,348,187, U.S. Pat. No. 6,171,611, U.S. Pat. No. 6,165,494, U.S. Pat. No. 6,117,417, U.S. Pat. No. 5,993,785, U.S. Pat. No. 5,695,746, U.S. Pat. No. 5,470,561, each of which is herein specifically incorporated by reference into this section of the specification and all other sections of the specification.

Oral formulations can also take the form of a lozenge, a treated substrate such as a topical swab or pad, that comprises the clay, or a buccal patch or other bioadhesive polymeric compositions comprising the clay. Lozenges are typically discoid-shaped solids containing the clay in a suitably flavored base. The base may be a hard sugar candy, glycerinated gelatin, or the combination of sugar with sufficient gelatin to give it form. Lozenges are placed in the mouth where they slowly dissolve, liberating the clay for direct contact with the affected mucosa. Lozenges can be prepared, for example, by adding water slowly to a mixture of the powdered clay along with excipients such as a sugar and a gum until a pliable mass is formed. The mass is rolled out and the lozenge pieces cut from the flattened mass, or the mass can be rolled into a cylinder and divided. Each cut or divided piece is shaped and allowed to dry, to thus form the lozenge dosage form.

Bioadhesive compositions are particularly suitable for treating oral mucositis. Buccal patches comprising a polymer and the clay, where the polymer becomes adhesive in the presence of saliva, are known in the art. Nonlimiting examples of biocompatible polymers that can be used to make a bioadhesive composition include polyethers, such as polyoxyalkylene block copolymers; cellulosic polymers (including hydroxypropylmethyl cellulose, hydroxymethyl cellulose, hydroxypropyl cellulose, methyl cellulose and ethylhydroxyethyl cellulose); gelatin; polyethylene glycol; polyacrylic acid (such as Carbopol™ gel); and glycerol (glycerin). More than one of these exemplary polymers may be included in the composition to provide the desired characteristics and other biocompatible polymers or other additives may also be included in the composition to the extent the inclusion is not inconsistent with performance requirements of the composition.

Optional Additives

The composition may also include conventional additives such as adhesive agents, antioxidants, crosslinking or curing agents, pH regulators, pigments, dyes, refractive particles, conductive species, antimicrobial agents, active agents and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the composition.

Non-limiting examples of suitable excipients, diluents, and carriers include: fillers and extenders such as starch, sugars, mannitol, and silicic derivatives; binding agents such as carboxymethyl cellulose and other cellulose derivatives, alginates, gelatin, and polyvinyl pyrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; carriers such as propylene glycol and ethyl alcohol, and lubricants such as talc, calcium and magnesium stearate, and solid polyethyl glycols.

Additives may be present in the compositions, such as flavoring, sweetening or coloring agents, or preservatives. Mint, such as from peppermint or spearmint, cinnamon, eucalyptus, citrus, cassia, anise and menthol are examples of suitable flavoring agents. Flavoring agents are preferably present in the oral compositions in an amount in the range of from 0 to 3%; preferably up to 2%, such as up to 0.5%, preferably around 0.2%, in the case of liquid compositions. Sweeteners include artificial or natural sweetening agents, such as sodium saccharin, sucrose, glucose, saccharin, dextrose, levulose, lactose, mannitol, sorbitol, fructose, maltose, xylitol, thaumatin, aspartame, D-tryptophan, dihydrochalcones, acesulfame, and any combinations thereof, which may be present in an amount in the range of from 0 to 2%, preferably up to 1% w/w, such as 0.05 to 0.3% w/w of the oral composition.

Other optional ingredients of oral aqueous compositions include humectants, surfactants (non-ionic, cationic or amphoteric), thickeners, gums and binding agents. A humectant adds body to the mouthspray formulation and retains moisture in a dentifrice composition. In addition, a humectant helps to prevent microbial deterioration during storage of the formulation. It also assists in maintaining phase stability and provides a way to formulate a transparent or translucent dentifrice. Suitable humectants include glycerine, xylitol, glycerol and glycols such as propylene glycol, which may be present in an amount of up to 50% w/w each, but total humectant is preferably not more than about 60-80% w/w of the composition. For example, liquid compositions may comprise up to about 30% glycerine plus up to about 5%, preferably about 2% w/w xylitol.

When the oral compositions are in the form of a mouth spray, it is preferred to include a film forming agent up to about 3% w/w of the oral composition, such as in the range of from 0 to 0.1%, preferably about 0.001 to 0.01%, such as about 0.005% w/w of the oral composition. Suitable film-formers include (in addition to sodium hyaluronate) those sold under the tradename Gantrez™.

Much of the foregoing description has been primarily directed to the treatment of oral mucositis. It should be recognized, however, that the same principles discussed above are also generally applicable to treatment of mucosal disorders occurring in other regions of the body, with the product form of the therapeutic composition being modified for administration to the other targeted mucosal site. For example, the therapeutic composition of the present disclosure is applicable for the prevention and/or treatment of mucosal disorders of the esophagus, vagina, bladder, urethra, and the gastrointestinal tract exclusive of the oral cavity, and in some embodiments of the gastrointestinal tract exclusive of the oral cavity, esophagus, rectum and anus. Mucositis at these other locations are mechanistically similar to oral mucositis, and particularly when the disorder is the result of chemotherapy or radiation therapy. For example, patients undergoing radiation therapy treatment for non-small cell lung cancer frequently develop esophagitis as a side effect of treatment.

The method of delivery to the affected region may be by any convenient technique as suitably adapted for the particular region of the body at issue. Some examples of possible product forms for administration of the therapeutic composition a gel formulated into a suppository would be one preferred product form for administration to treat mucosal surfaces of either the rectum or the vagina. A tablet, patch or film could be formulated to administer the therapeutic composition sublingually. A slurry or syrup as an oral solution could be used for treatment of mucosal surfaces in the esophagus and/or gastrointestinal tract. A bladder irrigation solution would be administered to the bladder by catheter. A spray would be advantageous in delivering the composition to either the nasal cavity or the lungs, while a droplet formulation would be advantageous for delivery to the eye or inner ear.

C. Exemplary Dosing Regimens and Patient Populations

In the studies conducted herein, the clay composition was applied topically to the areas of mucositis three times daily. It will be appreciated that this dosing regimen is merely exemplary, and the dosing schedule can be varied according to each individual, to the severity of mucositis, to the area of mucositis, and in accord with other parameters. By way of example, the clay formulation can be applied topically to mucosal surfaces of the oral cavity or gastro-intestinal tract, in some embodiments, one to eight applications per day can begin 24 hours before chemotherapy or radiation, and may continue after the conclusion of cancer treatment or other therapy associated with mucositis. By way of another example, the clay formulation can be administered to the desired local area, one, two, three, four, five or more times per day, and treatment can begin before or concurrent with chemotherapy and/or radiation, and may cease prior to the end of chemotherapy and/or radiation or may continue after chemotherapy and/or radiation has ended.

In one embodiment, the method is for treating or preventing oral mucositis, esophageal mucositis, or mucositis of the stomach, small intestine or large intestine resulting from radiation or chemotherapy for cancer. The method includes the step of administering to a patient an effective amount of a solution or suspension formed by placing one of the solid dosage forms containing therapeutic agent in an aqueous solution. The solution is administered as, for example, a mouth-rinse. Optionally, additional agents may be present in the solid dosage form.

In another embodiment, the method for treating or preventing oral mucositis esophageal mucositis, or mucositis of the stomach, small intestine or large intestine, or mucositis of the rectum or anus, resulting from radiation or chemotherapy for cancer includes the step of administering a solid dosage form described herein to the oral cavity of a patient, for example, sublingually, wherein clay comes into contact with the inflamed tissue.

Treatment according to the disclosed methods can begin prior to cancer treatment or other condition or therapy associated with mucositis (e.g., propylactically, and/or 1-2 days or up to 1 week prior), at or near the same time as cancer treatment or other therapy associated with mucositis (e.g., simultaneously with, within 1-4 hours of, or on the same day as the treatment), or shortly after the cessation of cancer treatment or other condition or therapy associated with mucositis (e.g., within 1-4 days of cessation, and/or prior to or upon appearance of symptoms). Treatment can then be maintained, for example, until any symptoms of mucositis have substantially cleared or the risk of developing such symptoms has passed. Thus, treatment started before or at or near the same time as cancer treatment or other condition or therapy associated with mucositis can be maintained, e.g., for 1-3, e.g., 1-2 days. In other examples, treatment is maintained for 1-4 or 2-3 weeks following the cessation of cancer treatment or other therapy associated with mucositis, as determined to be appropriate by one of skill in the art. In specific examples, the treatment according to the present disclosure is carried out only prior to cancer treatment or other therapy associated with mucositis (such as treatment of HIV/AIDS with chemotherapeutic agents or with antiretroviral agents with or without chemotherapeutic agents); prior to and concurrently with cancer treatment or other therapy associated with mucositis; prior to, concurrently with, and after cessation of cancer treatment or other therapy associated with mucositis; concurrently with cancer treatment or other therapy associated with mucositis only; concurrently with and after cessation of cancer treatment or other therapy associated with mucositis only; after cessation of cancer treatment or other therapy associated with mucositis only; or prior to and after cessation of cancer treatment or other therapy associated with mucositis only. Further, treatment according to the methods of the present disclosure can be altered, stopped, or re-initiated in a patient, depending on the status of any symptoms of mucositis. Treatment can be carried out at intervals determined to be appropriate by those of skill in the art. For example, the administration can be carried out 1, 2, 3, 4 or more times/day. It will be appreciated that the patients to be treated with the methods described herein are not limited to cancer patients, but include any patient that is at risk of or has developed mucositis, including HIV/AIDS patients being treated chemotherapeutic agents with or without antiretroviral agents.

Chemotherapeutic agents likely to cause oral mucositis include but are not limited to anthracyclines (such as daunorubicin, doxorubicin, pirubicin, idarubicin and mitoxantrone), methotrexate, dactinomycin, bleomycin, vinblastine, cytarabin, fluorouracil, mitramycine, etoposide, floxuridine, 5-fluorouracil, hydroxyurea, methotrexate, mitomycin, vincristine, vinorelbine, taxanes (such as docetaxel and paclitaxel), ifosfamide/eoposide, irinotecan, platinum, as well as combinations including one or more of these drugs. The risk of developing mucositis is markedly exacerbated when chemotherapeutic agents that typically produce mucosal toxicity are given in high doses, in frequent repetitive schedules, or in combination with ionizing irradiation (e.g., conditioning regimens prior to bone marrow transplant). The lesions induced by chemotherapeutic agents are clinically significant by about a week after treatment and the severity progresses to about day ten through twelve and begins to subside by day fourteen. Accordingly, in some embodiments, the patient to be treated is one undergoing or scheduled to undergo treatment with one or more of these chemotherapeutic agents.

Non-therapeutic radiation and/or chemical exposure, as may happen from accidents, acts of war, acts of civilian terrorism, space flights, or rescue and clean-up operations can also result in mucositis. In these scenarios the effects of radiation in the hematopoietic system and the gastrointestinal tract are critical. Furthermore, inflammation can be caused by conditions in the mouth itself, such as poor oral hygiene, dietary protein deficiency, poorly fitted dentures, or from mouth burns from hot food or drinks, toxic plants, or by conditions that affect the entire body, such as medications, allergic reactions, radiation therapy, or infections.

Combination Regimens and Combination Compositions

The methods presently disclosed can be used alone or in conjunction with other approaches to reducing the severity of mucositis. For example, the disclosed methods can be carried out in combination with antimicrobial or antifungal therapies, e.g., therapies involving administration of antibiotics such as nystatin, amphotericin, acyclovir, valacyclovir, clotimazole, and fluconazole. As a specific example of such treatment, patients with head and neck cancer receiving radiotherapy have colonization of the oropharyngeal region with gram-negative bacteria. Selective decontamination of the oral cavity with anti-microbial agents has the benefit of reducing oral mucositis associated with radiation therapy, but there may be limitations to the beneficial effects of such treatment. Anti-microbial therapy can kill bacteria, but cannot reduce endotoxin, and indeed may actually increase endotoxin. As endotoxin is a potent mediator of inflammation, it may contribute to the aggravation of mucositis and, thus, co-treatment with an antiendotoxin compound (e.g., a Lipid A analog, such as eritoran) and antibiotics can be used as a more effective approach to treating oral mucositis in such patients, according to the present disclosure.

The methods presently disclosed can also be used in conjunction with palliative therapies including the use of topical rinses, gels, or ointments that include lidocaine, articaine, and/or morphine, as well as other analgesic or anti-inflammatory agents. Specific examples of other agents and approaches that can be used in combination with TLR4 antagonists, according to the methods presently disclosed, include the following: palifermin (recombinant keratinocyte growth factor; rHuKGF; Kepivance™; Amgen) and AES-14 (uptake-enhanced L-glutamine suspension) (Peterson, *J. Support Oncol.* 4(2 Suppl. 1) 9-13, 2006); oral cryotherapy, low-level laser therapy, chlorhexidine, amifostine, hematologic growth factors, pentoxifylline, and glutamine (Saadeh, *Pharmacotherapy* 25(4):540-554, 2005); amifostine, antibiotic paste or pastille, hydrolytic enzymes, ice chips, benzydamine, calcium phosphate, honey, oral care protocols, povidone, and zinc sulphate (Worthington et al., *Cochrane Database Syst. Rev.* 2:CD000978, 2006); flurbiprofen (e.g., administered as a tooth patch; Stokman et al., *Support Care Cancer* 13(1):42-48, 2005); diphenhydramine, magnesium hydroxide/aluminum hydroxide, nystatin, and corticosteroids (Chan et al., *J. Oncol. Pharm. Pract.* 11(4):139-143, 2005); oral transmucosal fentanyl citrate (e.g., administered in the form of a lozenge; Shaiova et al., *Support Care Cancer* 12(4):268-273, 2004); clonazepam (e.g., in the form of a tablet; Gremeau-Richard et al., *Pain* 108(102):51-57, 2004); capsaicin (e.g., in the form of a lozenge; Okuno et al., *J. Cancer Integr. Med.* 2(3):179-183, 2004); ketamine (e.g., in the form of an oral rinse; Slatkin et al., *Pain Med.* 4(3):298-303, 2003); and granulocyte-macrophage colony-stimulating factor (GM-CSF)/granulocyte colony-stimulating factor (G-CSF), laser light therapy, and glutamine supplements (Duncan et al., *Aliment. Pharmacol. Ther.* 18(9):853-874, 2003).

An exemplary assay for the treatment of oral mucositis may be performed as described in the phase 3 clinical trial of Kepivance™ (palifermin) (see, Spielberger, *N. Engl. J. Med.*, 351(25):2590-2598 (2004)), or as described in phase II clinical trials of GM-CSF (molgramostin) (see McFleese et al., *Br. J. Radiol.* 79(943):608-13 (2006)).

In some embodiments, the patient is not undergoing, or has not undergone treatment with vitamin D.

In some embodiments of the present disclosure, the clay may be combined with a second therapeutic agent. In one embodiment, the second therapeutic agent is a pain reliever or anaesthetic, such as an anaesthetic found in a lozenge, spray or mouth rinse (e.g., phenol, benzocaine, phenazone, antipyrine, analgesine, dyclonine hydrochloride salt). In some embodiments, the pain reliever acts as a bactericidal and fungicidal in addition to acting as a local anaesthetic. In some embodiments, the pain reliever is an anaesthetic selected from the group consisting of fentanyl, hexylresorinol, dyclonine hydrochloride, asbenzocaine and phenol. For example, fentanyl has been approved for topical administration (transdermal patch), and is often used in cancer for pain control. In some embodiments, the clay is combined with fentanyl.

The Toll-like receptor (TLR) family plays a fundamental role in pathogen recognition and activation of innate immunity. Toll-like receptor 4 is a protein that in humans is encoded by the TLR4 gene. The TLR4 receptor detects lipopolysaccharide (LPS) from Gram-negative bacteria and is thus important in the activation of the innate immune system. TLR4 has also been designated as CD284 (cluster of differentiation 284). Examples of TLR4 agonists are: morphine, morphine-3-glucuronide, oxycodone, levorphanol, pethidine, fentanyl, methadone and buprenorphine.

According to the methods disclosed herein, a TLR4 antagonist can be administered to a patient before, during, and/or after treatment with a therapy that causes mucositis (e.g., oral or gastrointestinal mucositis) or puts the patient at risk of developing such mucositis. As is noted above, such treatments include radiation and chemotherapy, which act by blocking the growth of rapidly dividing cells, such as cancer cells and epithelial cells that line the surfaces of the gastrointestinal, respiratory, and genitourinary tracts. Specific examples of treatments that can lead to mucositis include radiation treatment (e.g., head and/or neck, whole body, targeted, and/or hyperfractionated radiation), as well as chemotherapeutic regimens used in the treatment of, or as adjuvant treatments for, conditions such as breast cancer, colon cancer, gastric cancer, genitourinary (e.g., bladder, prostate, or testicular) cancer, gynecologic (e.g., cervical, endometrial, ovarian, or uterine) cancer, head and neck/esophageal cancer, leukemia, lung (small cell or non small-cell) cancer, lymphoma (Hodgkin's or non-Hodgkin's), melanoma, multiple myeloma, pancreatic cancer, and sarcoma.

III. Examples

The following examples are given to illustrate the present disclosure. It should be understood that the claims are not to be limited to the specific conditions or details described in the examples.

Example 1

Acute Radiation Model of Mucositis

An acute radiation model in hamsters has proven to be an accurate, efficient and cost-effective technique to provide a preliminary evaluation of anti-mucositis compounds (Murphy, C. K. et al., (2008) *Clin Cancer Res.* 1(14):4292-7). The course of mucositis in this model is well-defined and results in peak scores approximately 14-16 Days following radiation. The acute model has little systemic toxicity, resulting in few hamster deaths, thus permitting the use of smaller groups (N=7-8) for initial efficacy studies. It has also been used to study specific mechanistic elements in the pathogenesis of mucositis. Molecules that show efficacy in the acute radiation model may be further evaluated in the more complex models of fractionated radiation, chemotherapy, or concomitant therapy.

Animals

Male LVG Syrian Golden Hamsters (Charles River Laboratories), aged 5 to 6 weeks, with average body weight of 89.5 g at study commencement, were used. Animals were individually numbered using an ear punch and housed in small groups of approximately 8 animals per cage. Animals were acclimatized prior to study commencement. During this period of 3 days, the animals were observed daily in order to reject animals that present in poor condition.

Housing and Diet

The study was performed in animal rooms provided with filtered air at a temperature of 70° F.+/−5° F. and 50%+/−20% relative humidity. Animal rooms were set to maintain a minimum of 12 to 15 air changes per hour. The room was on an automatic timer for a light/dark cycle of 12 hours on and 12 hours off with no twilight. Bed-O-Cobs® bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity was recorded during the study, and the records retained.

Animals were fed with a Purina Labdiet® 5053 rodent diet, and water was provided ad libitum.

Animal Randomization and Allocations.

Animals were randomly and prospectively divided into three (3) treatment groups prior to irradiation. Each animal was identified by an ear punch corresponding to an individual number. For more consistent identification, ear punch numbering was used rather than tagging, since tags may become dislodged during the course of the study. A cage card was used to identify each cage or label marked with the study number, treatment group number and animal numbers.

Weights and Survival

All animals were weighed daily and their survival recorded, in order to assess possible differences in animal weight among treatment groups as an indication for mucositis severity and/or possible toxicity resulting from the treatments.

Clay Composition

A dioctahedral smectite, calcium aluminosilicate clay with an average particle size of less than about 80 microns was mixed with deionized water to form a suspension of 10% w/v clay in water.

Mucositis Induction

Twenty-four male Syrian Golden Hamsters were randomly assigned to three equally-sized groups. On study day 0, mucositis was induced using a standardized acute radiation protocol. A single dose of radiation (40 Gy/dose) was administered to all animals on day 0. Radiation was generated with a 160 kilovolt potential (15-ma) source at a focal distance of 40 cm, hardened with a 0.35 mm Al filtration system. Irradiation targeted the left buccal pouch mucosa at a rate of 2.5 Gy/minute. Prior to irradiation, animals were anesthetized with an intraperitoneal injection of ketamine (160 mg/mL) and xylazine (8 mg/mL).

A composition comprising clay was given topically to the left cheek pouch three times daily either from Day 0 to Day 28 or from Day 7 to 28. The weight and general health of the animals were evaluated daily. Beginning on day 6 and continuing on alternate days for the duration of the study, oral mucositis was scored using a standard six point scale. The number of days of ulcerative mucositis was evaluated using a chi-squared test of mucositis scores of 3 or higher, and the individual daily group scores were assessed with a rank sum test. Mucositis in the left cheek pouch was evaluated clinically starting on Day 6, and continuing on alternate days until Day 28.

On Day 28, all animals were euthanized by $CO_2$ inhalation and death was confirmed by monitoring heartbeat in accordance with USDA guidelines.

TABLE 1-1

Study Design

| Group | Number of Animals | Treatment | Treatment Schedule | Dosing Volume (mL) |
|---|---|---|---|---|
| 1 | 8 males | Vehicle Control (WFI) | TID; Day 0 to 28 | 0.2 mL/Dose |
| 2 | 8 males | clay- 10% w/v | TID; Day 0 to 28* | 0.2 mL/Dose |
| 3 | 8 males | clay- 10% w/v | TID; Day 7 to 28 | 0.2 mL/Dose |

*The first dose of clay on Day 0 was administered 1-2 hours following radiation.

Mucositis Evaluation

The grade of mucositis was scored, beginning on day 6, and for every second day thereafter, through and including day 28. The effect on mucositis of each drug treatment compared to placebo was assessed. On each evaluation day, the number of animals with a blinded mucositis score of ≥3 in each drug treatment group was compared to the control group. Differences were compared on a cumulative basis and statistical significance was determined by chi-square analysis. Efficacy, in this analysis, is defined by a significant reduction in the number of days that a group of animals had ulcerations (scores ≥3) when compared to the control group.

Rank Sum Differences in Daily Mucositis Scores.

For each evaluation day the scores of the control group were compared to those of the treated groups using non-parametric rank sum analysis. Treatment success was considered as a statistically significant lowering of scores in the treated group on 2 or more days from day 6 to day 28.

ulceration (clinical scoring). In descriptive terms, this mucositis scoring scale is defined in Table 2-1, below.

TABLE 2-1

Scoring of Mucositis

| Score: | Description: |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth). |

A score of 1-2 is considered to represent a mild stage of the disease, whereas a score of 3-5 is considered to indicate moderate to severe mucositis. Following visual scoring, a digital image was taken of each animal's mucosa using a standardized technique. At the conclusion of the experiment, images were randomly numbered and scored by two independent trained observers graded the photographs in blinded fashion using the above-described scale (blinded scoring).

To examine the levels of clinically significant mucositis ("ulcerative mucositis"), as defined by presentation with open ulcers (score >3), the percentage of the number of animals presenting with an ulcer on each day of the study was determined. The percentage of animals in each group with an Oral Mucositis Score of 3 or higher on Days 6 to 28 is reported is shown in Table 2-2.

TABLE 2-2

Percent Ulceration by Day

| Group | Treatment Day | | | | | | | | | | | |
|---|---|---|---|---|---|---|---|---|---|---|---|---|
| | Day 6 | Day 8 | Day 10 | Day 12 | Day 14 | Day 16 | Day 18 | Day 20 | Day 22 | Day 24 | Day 26 | Day 28 |
| 1 (Control) | 0.0% | 0.0% | 0.0% | 0.0% | 62.5% | 100% | 100% | 100% | 75.0% | 62.5% | 37.5% | 37.5% |
| 2 (10% clay on days 0-28) | 0.0% | 0.0% | 0.0% | 0.0% | 25.0% | 87.5% | 75.0% | 75.0% | 75.0% | 62.5% | 75.0% | 87.5% |
| 3 (10% clay on days 7-28) | 0.0% | 0.0% | 0.0% | 12.5% | 62.5% | 87.5% | 87.5% | 87.5% | 87.5% | 87.5% | 87.5% | 50.0% |

Example 2

Evaluation of Mucositis in Animals Treated with Clay Composition

Using the twenty-four hamsters in study groups 1, 2, and 3, a mucositis score, weight change and survival were measured throughout the study period described above in Example 1. For the evaluation of mucositis, the animals were anesthetized with an inhalation anesthetic, and the left pouch everted. Mucositis was scored visually by comparison to a validated photographic scale, ranging from 0 for normal, to 5 for severe All eight (100%) of the vehicle control animals developed ulcerative mucositis by Day 16 and this ulceration persisted through 20 days after radiation. Meanwhile, in the groups treated with clay there was never a study day where all animals from either treatment group exhibited ulceration. The largest treatment effects were observed in the group treated with clay from Day 0 to 28. Here, the percent ulceration was reduced compared to vehicle control by 37.5% on Day 14, by 12.5% on Day 16, and by 25% on Days 18 and 20.

No deaths were observed during this study. The results of daily weight change are shown in FIGS. 1A-1B. The duration of mucositis is shown in Table 1 and FIGS. 2A-2B. The severity of mucositis is reported in Table 2.

Example 3

Binding of the Pro-Inflammatory Cytokine with a Clay Composition

A dioctahedral smectite, calcium aluminosilicate clay with an average particle size of less than about 80 microns was suspended in phosphate buffered saline at six different concentrations: 0.5 mg/mL, 1 mg/mL, 5 mg/mL, 10 mg/mL, 50 mg/mL, and 100 mg/mL.

Recombinant TNFα (50 mg/ml stock in 100% ddH$_2$O) was added to each of the clay samples to a final concentration of 1000 pg/mL TNFα. One sample of 1000 pg/mL TNFα in 100% PBS with no clay was prepared as a control. The samples were vortexed for 30 seconds and allowed to incubate at room temperature for 30 minutes. During this incubation the samples were vortexed again every 10 minutes for 5 seconds. After incubation, the samples were centrifuged at 10,000 rpm for 5 minutes and the supernatant was isolated.

Figure 3A:
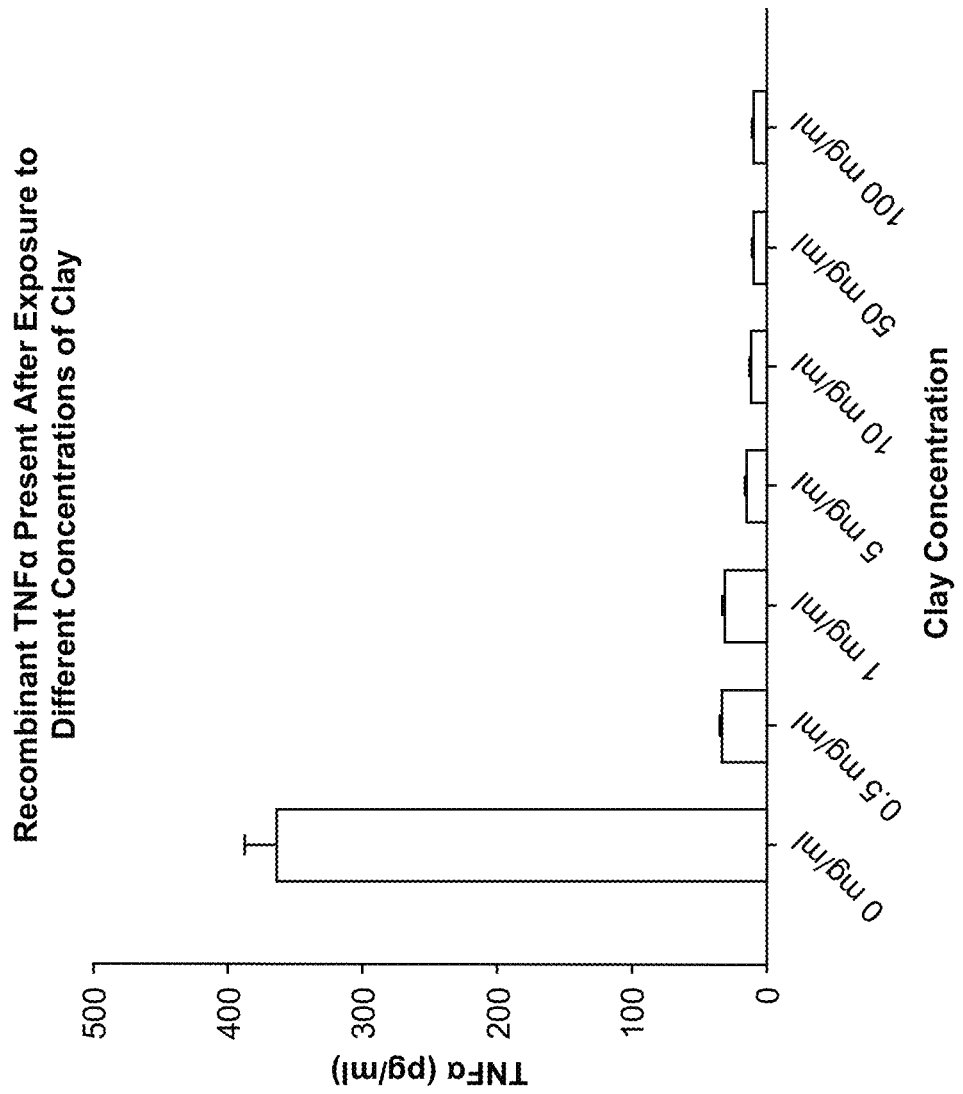
FIGS. 3A-3B are bar graphs showing the amount, in pg/mL of TNF-α present in solution after incubation with the noted concentrations of calcium aluminosilicate clay (FIG. 3A) and the percent of TNF-α relative to the control solution containing no clay for each of the clay solutions (FIG. 3B).
Figure 3B:
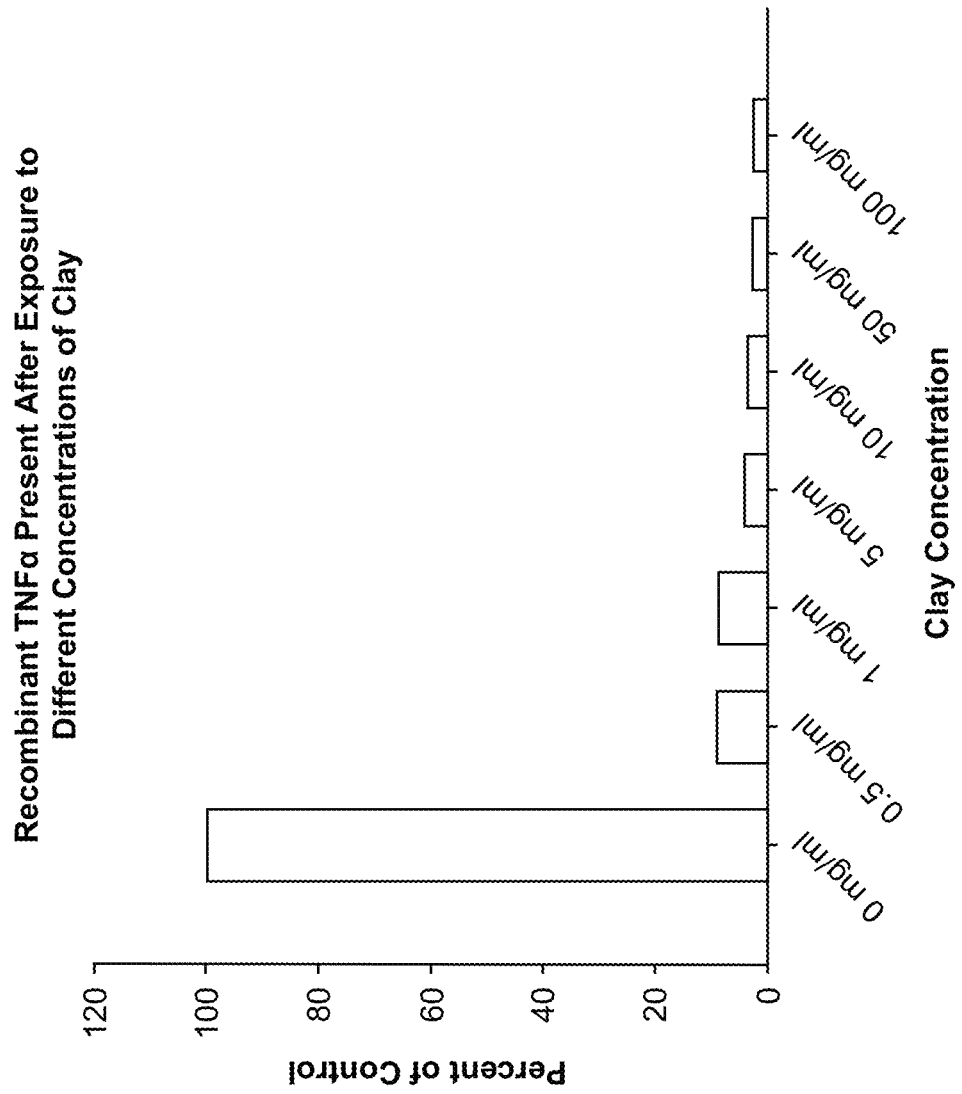

Follow the protocol on a TNFα ELISA kit (R&D Systems Inc.), the amount of TNF-alpha in each supernatant was examined. The results are shown in FIGS. 3A-3B.

While a number of exemplary aspects and embodiments have been discussed and illustrated, those of skill in the art will recognize certain modifications, permutations, additions and sub-combinations thereof which do not depart from the scope of the present disclosure. It is to be understood that the disclosure is not to be limited to the specific embodiments disclosed herein, as such are presented by way of example. It is therefore intended that the following appended claims and claims hereafter introduced are interpreted to include all such modifications, permutations, additions and sub-combinations as are within their true spirit and scope.

All literature and similar materials cited in this application, including, but not limited to, patents, patent applications, articles, books, treatises, internet web pages and other publications cited in the present disclosure, regardless of the format of such literature and similar materials, are expressly incorporated by reference in their entirety for any purpose to the same extent as if each were individually indicated to be incorporated by reference. In the event that one or more of the incorporated literature and similar materials differs from or contradicts the present disclosure, including, but not limited to defined terms, term usage, described techniques, or the like, the present disclosure controls.

The invention claimed is:

1. A method for treating esophageal or gastrointestinal mucositis, comprising:
    administering by ingestion to the esophagus or gastrointestinal tract of a subject a therapeutically effective amount of a composition comprising a clay having an average particle size of 100 microns or greater, wherein the clay is a low-swelling or a non-swelling, calcium clay species, and wherein the administering is prior to or concurrent with initiation of radiation therapy in a cancer subject.

2. The method of claim 1, wherein the clay is a smectite clay.

3. The method of claim 1, wherein the clay is a calcium montmorillonite clay.

4. The method of claim 1, wherein the administering further comprises administering to a subject undergoing or planning to undergo chemotherapy.

5. The method of claim 1, wherein the administering continues for the duration of radiation therapy.

6. The method of claim 1, wherein the administering comprises administering more than once daily.

7. The method of claim 1, wherein the administering comprises administering once daily.

8. The method of claim 1, wherein the administering comprises administering orally a fluid comprising the clay.

9. The method of claim 8, wherein the fluid is a solution, a suspension, a paste, or a gel.

10. The method of claim 1, wherein the administering comprises administering a composition comprising a polymer.

11. The method of claim 10, wherein the composition is a bioadhesive polymer.

12. The method of claim 1, wherein the administering comprises administering a solid dosage form that disintegrates in an aqueous medium.

13. The method of claim 12, wherein the aqueous medium is a body fluid.

14. The method of claim 1, wherein the subject is concurrently treated with at least one therapeutic agent.

15. The method of claim 14, wherein the therapeutic agent is a pain reliever, a chemotherapeutic, an anti-inflammatory or antibiotic.

16. The method of claim 1, further comprising, prior to said administering, contacting a clay with a fluid to form a composition suitable for ingestion.

17. A method for reducing severity of esophageal or gastrointestinal mucositis, comprising:
    administering by ingestion to the esophagus or gastrointestinal tract of a subject a therapeutically effective amount of a composition comprising a clay having an average particle size of 100 microns or greater, wherein the clay is a low-swelling or a non-swelling, calcium clay species, and wherein the administering is prior to or concurrent with initiation of radiation therapy in a cancer subject.

* * * * *